(12) United States Patent
Schramm et al.

(10) Patent No.: US 7,741,295 B2
(45) Date of Patent: *Jun. 22, 2010

(54) SIR2 PRODUCTS AND ACTIVITIES

(75) Inventors: Vern L. Schramm, New Rochelle, NY (US); Jef D. Boeke, Baltimore, MD (US); Anthony Sauvé, Bronx, NY (US); Ivana Celic, Baltimore, MD (US)

(73) Assignees: Albert Einstein College of Medicine of Yeshiva University, Bronx, NY (US); The Johns Hopkins University, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 12/231,880

(22) Filed: Sep. 5, 2008

(65) Prior Publication Data

US 2009/0068695 A1   Mar. 12, 2009

Related U.S. Application Data

(60) Continuation of application No. 11/248,523, filed on Oct. 12, 2005, now Pat. No. 7,432,246, which is a division of application No. 10/301,514, filed on Nov. 21, 2002, now Pat. No. 6,987,091.

(60) Provisional application No. 60/331,919, filed on Nov. 21, 2001.

(51) Int. Cl.
A61K 31/70 (2006.01)
A01N 43/04 (2006.01)

(52) U.S. Cl. ............... 514/23; 514/12; 514/13; 514/14; 514/18; 536/26.1; 536/23.2; 536/124; 536/23.1; 536/55.3; 435/90; 435/252.3; 435/320.1; 435/254.11; 435/358; 435/364; 424/277.1; 530/322; 530/345

(58) Field of Classification Search ............... None
See application file for complete search history.

(56) References Cited

U.S. PATENT DOCUMENTS

| 4,495,180 | A | 1/1985 | Alexander |
| 5,658,890 | A | 8/1997 | Pankiewicz et al. |
| 6,987,091 | B2 | 1/2006 | Schramm et al. |
| 7,432,246 | B2 | 10/2008 | Schramm et al. |
| 2006/0292652 | A1 | 12/2006 | Curtis et al. |

FOREIGN PATENT DOCUMENTS

| WO | WO 02/38579 A1 | 5/2002 |
| WO | WO 2005/016342 | 2/2005 |

OTHER PUBLICATIONS

Challis, B. C., et al., The alkyl halide catalysed pseudomolecular rearrangements of imidates to amides: an explanation for the ambident nucleophilic properties of neutral amides. J. Chem. Soc. Perkin II, 192-197 (1978).

Frye, R. A. Characterization of five human cDNAs with homology to the yeast SIR2 gene: Sir2-like proteins (sirtuins) metabolize NAD and may have protein ADP-ribosyltransferase activity. Biochem. Biophys. Res. Commun. 260, 273-9 (1999).
Imai, S., et al., Transcriptional silencing and longevity protein Sir2 is an NAD- dependent histone deacetylase. Nature 403, 795-800 (2000).
Landry, J., et al., Role of NAD(+) in the deacetylase activity of the SIR2-like proteins. Biochem. Biophys. Res. Commun. 278, 685-90 (2000).
Landry, J., et al., The silencing protein SIR2 and its homologs are NAD-dependent protein deacetylases. Proc. Natl. Acad. Sci. U.S.A. 97, 5807-11 (2000).
Min, J., et al., Crystal structure of a SIR2 homolog-NAD complex. Cell 105, 269-79 (2001).
Moazed, D., Enzymatic activities of Sir2 and chromatin silencing. Curr. Opin. Cell Biol. 13, 232-8 (2001).
Scheuring, J., et al., Transition-state structure for the ADP-ribosylation of recombinant Gialpha1 subunits by pertussis toxin. Biochemistry 37, 2748-58 (1998).
Smith, J. S., et al., A phylogenetically conserved NAD+-dependent protein deacetylase activity in the Sir2 protein family. Proc. Natl. Acad. Sci. U.S.A. 97, 6658-63 (2000).
Borch, R. F., A new method for the reduction of secondary and tertiary amides. Tetrahedron. Lett. 1, 61-65 (1968).
Smith, J. S., et al., SIR2 family of NAD+-dependent protein deacetylases. Meth. Enzymol. 353, 282-300 (2002).
Takayama, S., et al., Selective Inhibition of Beta-1, 4- and Alpha-1, 3-Galactosyltransferases: Donor Sugar-Nucleotide Based Approach. Bioorganic & Medicinal Chemistry, 7(2), 401-409 (1999).
Tanner, K., et al., Silent information regulator 2 family of NAD-dependent histone/protein deacetylases generates a unique product, 1-O-acetyl-ADP-ribose. Proc. Natl. Acad. Sci. U.S.A. 97, 14178-82 (2000).
Tanny, J. C., et al., Coupling of histone deacetylation to NAD breakdown by the yeast silencing protein Sir2: Evidence for acetyl transfer from substrate to an NAD breakdown product. Proc. Natl. Acad. Sci. U.S.A. 98, 415-20 (2001).
Vaziri et al., hSIR2 Functions as an NAD-Dependent p53 Deacetylase, Cell 107:149-159 (2001).
Yost, D., et al., Adenosine diphophoribose transfer reactions catalyzed by Bungarus fasciatus venom NAD glycohydrolase, J. Biological Chem., 258(5), 3075-3080 (1983).
Tanny J. C., et al., An Enzymatic Activity in the Yeast Sir2 Protein that is Essential for Gene Silencing. Cell, Dec. 23, 1999, vol. 99, No. 7, pp. 735-45.
Minor et al., Synthesis of 2- and 6-fluoronicotinamides, Journal of the American Chemical Society, 1949, vol. 71, pp. 1125-1126, Abstract. Chem. Abstract Accession No. 1949:22614.
Lee, Susan et al., Quantification of endogenous sirtuin metabolite O-acetyl-ADP-ribose, Analytical Biochemistry 383, pp. 174-179, 2008 Elsevier Inc.

*Primary Examiner*—Patrick T Lewis
(74) *Attorney, Agent, or Firm*—Amster, Rothstein & Ebenstein LLP

(57) ABSTRACT

A novel compound, 2'/3'-O-acetyl-ADP-ribose, is provided. The compound is a mixture of the 2' and 3' regioisomers of O-acetyl-ADP ribose, and is formed nonenzymatically from 2'-O-acetyl-ADP-ribose, which is the newly discovered product of the reaction of Sir2 enzymes with acetylated peptides and NAD$^+$. Analogs of 2'/3'-O-acetyl-ADP-ribose are also provided. Additionally, methods of preparing 2'/3'-O-acetyl-ADP-ribose, methods of determining whether a test compound is an inhibitor of a Sir2 enzyme, methods of detecting Sir2 activity in a composition, methods of deacetylating an acetylated peptide, and methods of inhibiting the deacetylation of an acetylated peptide are provided. Prodrugs of 2'/3'-O-acetyl-ADP-ribose are also provided.

24 Claims, 13 Drawing Sheets

2'/3'-O-AADPR

SIR2 PRODUCTS AND ACTIVITIES

CROSS-REFERENCE TO RELATED APPLICATIONS

This application is a continuation of U.S. patent application Ser. No. 11/248,523, filed Oct. 12, 2005, now U.S. Pat. No. 7,432,246 B2, which is a divisional of U.S. patent application Ser. No. 10/301,514, filed Nov. 21, 2002, now U.S. Pat. No. 6,987,091, which claims benefit of U.S. Provisional Application No. 60/331,919, filed Nov. 21, 2001, the contents of all of which are hereby incorporated by reference in their entirety.

STATEMENT REGARDING FEDERALLY SPONSORED RESEARCH

This invention was made with U.S. Government support under National Institutes of Health Grant No. AI 34342. The Government has certain rights to the invention.

BACKGROUND (1) Field of the Invention

The present invention generally relates to enzyme products and activities. More particularly, the invention is directed to the discovery of products and activities of Sir2 enzymes.

(2) Description of the Related Art

REFERENCES CITED

1. Brachmann, C. B., Sherman, J. M., Devine, S. E., Cameron, E. E., Pillus, L., and Boeke, J. D. The SIR2 gene family, conserved from bacteria to humans, functions in silencing, cell cycle progression, and chromosome stability. *Genes Dev.* 9, 2888-90 (1995).
2. Frye, R. A. Characterization of five human cDNAs with homology to the yeast SIR2 gene: Sir2-like proteins (sirtuins) metabolize NAD and may have protein ADP-ribosyltransferase activity. *Biochem. Biophys. Res. Commun.* 260, 273-9 (1999).
Moretti, P., Freeman, K., Coodly, L., and Shore, D. Evidence that a complex of SIR proteins interacts with the silencer and telomere-binding protein RAP1. *Genes Dev.* 8, 2257-69. (1994).
4. Rine, J., and Herskowitz, I. Four genes responsible for a position effect on expression from HML and HMR in *Saccharomyces cerevisiae*. *Genetics* 116, 9-22 (1987).
5. Shou, W., Seol, J. H., Shevchenko, A., Baskerville, C., Moazed, D., Chen, Z. W., Jang, J., Charbonneau, H., and Deshaies, R. J. Exit from mitosis is triggered by Tem1-dependent release of the protein phosphatase Cdc14 from nucleolar RENT complex. *Cell* 97, 233-44 (1999).
6. Straight, A. F., Shou, W., Dowd, G. J., Turck, C. W., Deshaies, R. J., Johnson, A. D., and Moazed, D. Net1, a Sir2-associated nucleolar protein required for rDNA silencing and nucleolar integrity. *Cell* 97, 245-56 (1999).
7. Hecht, A., Laroche, T., Strahl-Bolsinger, S., Gasser, S. M., and Grunstein, M. Histone H3 and H4N-termini interact with SIR3 and SIR4 proteins: a molecular model for the formation of heterochromatin in yeast. *Cell* 80, 583-92 (1995).
8. Johnson, L. M., Kayne, P. S., Kahn, E. S., and Grunstein, M. Genetic evidence for an interaction between SIR3 and histone H4 in the repression of the silent mating loci in *Saccharomyces cerevisiae*. *Proc. Natl. Acad. Sci. U.S.A.* 87, 6286-90 (1990).
9. Braunstein, M., Rose, A. B., Holmes, S. G., Allis, C. D., and Broach, J. R. Transcriptional silencing in yeast is associated with reduced nucleosome acetylation. *Genes Dev.* 7, 592-604 (1993).
10. Imai, S., Armstrong, C. M., Kaeberlein, M., and Guarente, L. Transcriptional silencing and longevity protein Sir2 is an NAD-dependent histone deacetylase. *Nature* 403, 795-800 (2000).
11. Landry, J., Sutton, A., Tafrov, S. T., Heller, R. C., Stebbins, J., Pillus, L., and Sternglanz, R. The silencing protein SIR2 and its homologs are NAD-dependent protein deacetylases. *Proc. Natl. Acad. Sci. U.S.A.* 97, 5807-11 (2000).
12. Smith, J. S., Brachmann, C. B., Celic, I., Kenna, M. A., Muhammad, S., Starai, V. J., Avalos, J. L., Escalante-Semerena, J. C., Grubmeyer, C., Wolberger, C., and Boeke, J. D. A phylogenetically conserved NAD+-dependent protein deacetylase activity in the Sir2 protein family. *Proc. Natl. Acad. Sci. U.S.A.* 97, 6658-63 (2000).
13. Tsang, A. W., and Escalante-Semerena, J. C. CobB, a new member of the SIR2 family of eucaryotic regulatory proteins, is required to compensate for the lack of nicotinate mononucleotide: 5,6-dimethylbenzimidazole phosphoribosyltransferase activity in cobT mutants during cobalamin biosynthesis in *Salmonella typhimurium* LT2. *J. Biol. Chem.* 273, 31788-94 (1998).
14. Landry, J., Slama, J. T.; and Sternglanz, R. Role of NAD (+) in the deacetylase activity of the SIR2-like proteins. *Biochem. Biophys. Res. Commun.* 278, 685-90 (2000).
15. Tanner, K. G., Landry, J., Sternglanz, R., and Denu, J. M. Silent information regulator 2 family of NAD-dependent histone/protein deacetylases generates a unique product, 1-O-acetyl-ADP-ribose. *Proc. Natl. Acad. Sci. U.S.A.* 97, 14178-82 (2000).
16. Tanny, J. C., and Moazed, D. Coupling of histone deacetylation to NAD breakdown by the yeast silencing protein Sir2: Evidence for acetyl transfer from substrate to an NAD breakdown product. *Proc. Natl. Acad. Sci. U.S.A.* 98, 415-20 (2001).
17. Moazed, D. Enzymatic activities of Sir2 and chromatin silencing. *Curr. Opin. Cell Biol.* 13, 232-8 (2001).
18. Min, J., Landry, J., Sternglanz, R., and Xu, R. M. Crystal structure of a SIR2 homolog-NAD complex. *Cell* 105, 269-79 (2001).
19. Smith, J. S., Avalos, J., Celic, I., Muhammad, S., Wolberger, C., and Boeke, J. D. The SIR2 family of NAD$^+$-dependent protein deacetylases. *Meth. Enzymol.* 342, in press (2001).
20. Gu, W., and Roeder, R. G. Activation of p53 sequence-specific DNA binding by acetylation of the p53 C-terminal domain. *Cell* 90, 595-606. (1997).
21. Abraham, J., Kelly, J., Thibault, P., and Benchimol, S. Post-translational modification of p53 protein in response to ionizing radiation analyzed by mass spectrometry. *J. Mol. Biol.* 295, 853-64 (2000).
22. Liu, L., Scolnick, D. M., Trievel, R. C., Zhang, H. B., Marmorstein, R., Halazonetis, T. D., and Berger, S. L. p53 sites acetylated in vitro by PCAF and p300 are acetylated in vivo in response to DNA damage *Mol. Cell. Biol.* 19, 1202-9 (1999).
23. Sakaguchi, K., Herrera, J. E., Saito, S., Miki, T., Bustin, M., Vassilev, A., Anderson, C. W., and Appella, E. DNA damage activates p53 through a phosphorylation-acetylation cascade. *Genes Dev.* 12, 2831-41 (1998).
24. Sterner, D. E., and Berger, S. L. Acetylation of histones and transcription-related factors. *Microbiol. Mol. Biol. Rev.* 64, 435-59 (2000).

25. Cervantes-Laurean, D., Jacobson, E. L., and Jacobson, M. K. Preparation of Low Molecular Weight Model Conjugates for ADP-Ribose Linkages to protein. *Methods Enzymol.* 280, 275-87 (1997).
26. Muller-Steffner, H. M., Malver, O., Hosie, L., Oppenheimer, N. J., and Schuber, F. Slow-binding inhibition of NAD+ glycohydrolase by arabino analogues of beta-NAD. *J. Biol. Chem.* 267, 9606-11 (1992).
27. Sauve, A. A., Deng, H. T., Angeletti, R. H., and Schramm, V. L. A covalent intermediate in CD38 is responsible for ADP-ribosylation and cyclization reactions. *J. Amer. Chem. Soc.* 122, 7855-7859 (2000).
28. Gottschling, D. E. Gene silencing: two faces of SIR2. *Curr. Biol.* 10, R708-11 (2000).
29. Lin, S. J., Defossez, P. A., and Guarente, L. Requirement of NAD and SIR2 for life-span extension by calorie restriction in *Saccharomyces cerevisiae*. *Science* 289, 2126-8 (2000).
30. Tissenbaum, H. A., and Guarente, L. Increased dosage of a sir-2 gene extends lifespan in *Caenorhabditis elegans*. *Nature* 410, 227-30 (2001).
31. Guarente, L. Sir2 links chromatin silencing, metabolism, and aging. *Genes Dev.* 14, 1021-6 (2000).
32. Cuperus, G., Shafaatian, R., and Shore, D. Locus specificity determinants in the multifunctional yeast silencing protein Sir2. *Embo. J.* 19, 2641-51 (2000).
33. Gotta, M., Strahl-Bolsinger, S., Renauld, H., Laroche, T., Kennedy, B. K., Grunstein, M., and Gasser, S. M. Localization of Sir2p: the nucleolus as a compartment for silent information regulators. *Embo. J.* 16, 3243-55 (1997).
34. Afshar, G., and Murnane, J. P. Characterization of a human gene with sequence homology to *Saccharomyces cerevisiae* SIR2. *Gene* 234, 161-8 (1999).
35. Perrod, S., Cockell, M. M., Laroche, T., Renauld, H., Ducrest, A. L., Bonnard, C., and Gasser, S. M. A cytsolic NAD-dependent deacetylase, Hst2p, can modulate nucleolar and telomeric silencing in yeast. *Embo. J.* 20, 197-209 (2001).
36. Yang, Y. H., Chen, Y. H., Zhang, C. Y., Nimmakayalu, M. A., Ward, D. C., and Weissman, S. Cloning and characterization of two mouse genes with homology to the yeast Sir2 gene. *Genomics* 69, 355-69 (2000).
37. Murphy, M., Ahn, J., Walker, K. K., Hoffman, W. H., Evans, R. M., Levine, A. J., and George, D. L. Transcriptional repression by wild-type p53 utilizes histone deacetylases, mediated by interaction with mSin3a. *Genes Dev.* 13, 2490-501 (1999).
38. Juan, L. J., Shia, W. J., Chen, M. H., Yang, W. M., Seto, E., Lin, Y. S., and Wu, C. W. Histone deacetylases specifically down-regulate p53-dependent gene activation. *J. Biol. Chem.* 275, 20436-43 (2000).
39. Rising, K., and Schramm, V. L. Transition state analysis of NAD+ hydrolysis by the cholera toxin catalytic subunit. *J. Am. Chem. Soc.* 119, 27-37 (1997).
40. Borch, R. F. A new method for the reduction of secondary and tertiary amides. *Tetrahedron Lett.* 1, 61-65 (1968).
41. Challis, B. C., and Frenkel, A. D. The alkylhalide catalyzed pseudomolecular rearrangements of imidates to amides: an explanation for the ambient nucleophilic properties of neutral amides. *J. Chem. Soc. Perkin* 11, 192-197 (1978).
42. Scheuring, J., Berti, P. J., and Schramm, V. L. Transition-state structure for the ADP-ribosylation of recombinant $G_{ialpha1}$ subunits by pertussis toxin. *Biochemistry* 37, 2748-58 (1998).
43. Munshi, C. B., Fryxell, K. B., Lee, H. C., and Branton, W. D. Large-scale production of human CD38 in yeast by fermentation. *Methods Enzymol.* 280, 318-30 (1997).
44. Sleath, P. R., Handlon, A. L., and Oppenheimer, N. J. Pyridine coenzyme analogs 3. Synthesis of three NAD+ analogs containing a 2'-deoxy-2'-substituted nicotinamide arabinosyl moiety. *J. Org. Chem.* 56, 3608-3613 (1991).
45. Rustandi, R. R., Baldisseri, D. M., and Weber, D. J. Structure of the negative regulatory domain of p53 bound to S100B(betabeta). *Nat. Struct. Biol.* 7, 570-4 (2000).
46. Luo, J., Nikolaev, A. Y., Imai, S., Chen, D., Su, F., Shiloh, A., Guarente, L., and Gu, W. Negative control of p53 by Sir2α promotes cell survival under stress. *Cell* 107, 137-48 (2001).
47. Khamnei, S., and Torrence, P. F. Neighboring group catalysis in the design of nucleotide prodrugs. *J. Med. Chem.* 39, 4109-15 (1996).

The Sir2p-like enzymes are broadly conserved from bacteria to humans[1,2]. In yeast, these proteins form complexes with other proteins to silence chromatin[3,6] by accessing histones[7,8] and deacetylating them[9-12]. Sir2 enzymes are homologs of the bacterial enzyme cobB, a phosphoribosyl-transferase[13], which led to the finding that Sir2p employs $NAD^+$ as a co-substrate in deacetylation reactions[10,14,12]. This unusual requirement for $NAD^+$ is stoichiometric[14] and generates a novel product originally proposed to be β-1'-AADPR[15,16] or possibly 2'-AADPR[16,17]. A crystal structure of a Sir2p homolog from *Archaeoglobus fulgidus* called Sir2-Af1 was recently determined with $NAD^+$ bound at the active site. The structure was interpreted in the context of a catalytic mechanism that produces β-1'-AADPR[18]. A cleft is proposed to bind the acetyl-lysine side chain of substrate proteins in proximity to the C1' of the bound $NAD^+$, providing substrate organization for acetyl group transfer between the peptide side chain and $NAD^{+18}$.

From mechanistic and thermodynamic considerations, the $NAD^+$ dependent deacetylation by Sir2p is an unusual reaction, since Lys N-deacetylation reactions are simple to accomplish by hydrolysis alone. The apparent coupling of hydrolysis and ADP-ribose transfer to acetate forms acetyl-ADP-ribose (AADPR) as product, and generates a new metabolite of unknown function[15-17].

Evidence to date indicates that histones are in vivo substrates of Sir2 enzymes. Yet, the genomes of eubacteria such as *Salmonella* which lack histones, encode Sir2-like proteins[19]. Similarly, archaeal genomes that encode Sir2ps also encode histone-like proteins, but those histones lack the N-terminal tails that are the prominent sites of lysine acetylation in eukaryotic histones. One archaeal species, *Archaeoglobus fulgidus*, encodes two different Sir2-like deacetylases that are 47% identical and the X-ray structure of one of these (Sir2Af1) was recently determined[18]. Sir2Af2 has been characterized more extensively biochemically, and is active in vitro on defined substrates[12].

Histone deacetylation by Sir2p is proposed to be the major reaction that converts chromatin from active to silent states[9,10,12]. This suggestion is supported by studies of silencing complexes which show Sir21) protein is the only conserved SIR family member in all yeast silencing complexes studied[28]. Caloric restriction upregulates Sir2p activity and may extend lifespan, showing that silencing might have potent biological effects in various organisms[29,30]. The requirement for $NAD^+$ and evidence that silencing factors can "sense" the redox state of the cell suggests that Sir2p family members are unique amide-hydrolysis enzymes with broad roles[12,31].

The distribution of Sir2p family of enzymes into organisms without histone substrates, and eukaryotic genomes encoding multiple Sir2 proteins, suggest a family of deacetylases with varying substrates. Mutagenesis experiments suggest that the N- and C-terminal regions flanking the catalytic core domain of Sir2p help direct it to different targets[32]. Although most Sir2 proteins in eukaryotic cells are located in the nucleus[33] others are cytosolic[34,36], or even mitochondrial (Onyango, Celic, Boeke and Feinberg; unpublished observations) which suggests additional substrates.

SUMMARY OF THE INVENTION

The present invention is based on two discoveries. The first discovery is the determination that a product of the reaction of a Sir2 with an acetylated peptide and NAD+ is 2'-O-acetyl-ADP-ribose. The 2' acetyl group can isomerize with the 3' hydroxyl, with the reverse isomerization occurring more slowly, until an equilibrium is formed between the 2' and 3' forms. Thus, the Sir2 reaction ultimately causes the production of 2'/3'-O-acetyl-ADP-ribose (FIG. 10).

The second discovery is that Sir2 enzymes deacetylate peptides other than histones. Examples of such peptides are acetylated p53 and fragments thereof. Based on experimental results described in Example 1, the skilled artisan would expect that Sir2 enzymes deacetylate any acetylated peptide of at least two amino acids, wherein at least one of the amino acids comprises a lysine residue that is acetylated at the ε-amino moiety.

Accordingly, the present invention is directed to purified preparations of 2'/3'-O-acetyl-ADP-ribose, and analogs thereof that exhibit increased stability in cells.

The present invention is also directed to methods of preparing 2'/3'-O-acetyl-ADP-ribose. The methods comprise combining a Sir2 enzyme with NAD+ and an acetylated peptide substrate of Sir2 in a reaction mixture under conditions and for a time sufficient to deacetylate the peptide, then identifying and purifying the 2'/3'-O-acetyl-ADP-ribose from the reaction mixture.

Additionally, the present invention is directed to methods of determining whether a test compound is an inhibitor of a Sir2 enzyme. The methods comprise combining the test compound with the Sir2 enzyme, NAD+ and an acetylated peptide substrate of Sir2 under conditions and for a time sufficient to deacetylate the peptide in the absence of the test compound, quantifying 2'/3'-O-acetyl-ADP-ribose produced from the acetylated peptide, then comparing the quantity of 2'/3'-O-acetyl-ADP-ribose produced with a quantity of 2'/3'-O-acetyl-ADP-ribose produced under the same conditions but without the test compound. In these methods, the presence of less 2'-O-acetyl-ADP-ribose and/or 3'-O-acetyl-ADP-ribose than without the test compound indicates that the test compound is an inhibitor of the Sir2 enzyme.

In other embodiments, the present invention is directed to methods of detecting activity of a Sir2 in a composition. The methods comprise combining the composition with NAD+ and an acetylated peptide substrate of a Sir2 under conditions and for a time sufficient to deacetylate the peptide in the presence of Sir2 activity, then measuring 2'/3'-O-acetyl-ADP-ribose. The presence of 2'/3'-O-acetyl-ADP-ribose indicates the presence of Sir2 activity in the composition.

The present invention is additionally directed to methods of deacetylating an acetylated peptide. The methods comprise combining the peptide with a Sir2 enzyme. In novel aspects of these embodiments, the acetylated peptide is not a histone.

Additionally, the present invention is directed to methods of inhibiting the deacetylation of an acetylated peptide. The methods comprise mixing the acetylated peptide with 2'/3'-O-acetyl-ADP-ribose or an analog thereof.

In additional embodiments, the invention is directed to prodrugs of 2'/3'-O-acetyl-ADP-ribose. The prodrugs comprise 2'/3'-O-acetyl-ADP-ribose covalently bonded to a moiety by an esterase-sensitive bond. In these embodiments, the prodrug is capable of passing into a cell more easily than 2'/3'-O-acetyl-ADP-ribose.

The acetyl moiety can be placed in the proper attack geometry to form an acyl-O—C1' bond with α stereochemistry. The p53 C-terminal peptide containing N-acetylated lysine 382 is a schematic model only.

Figure 7:
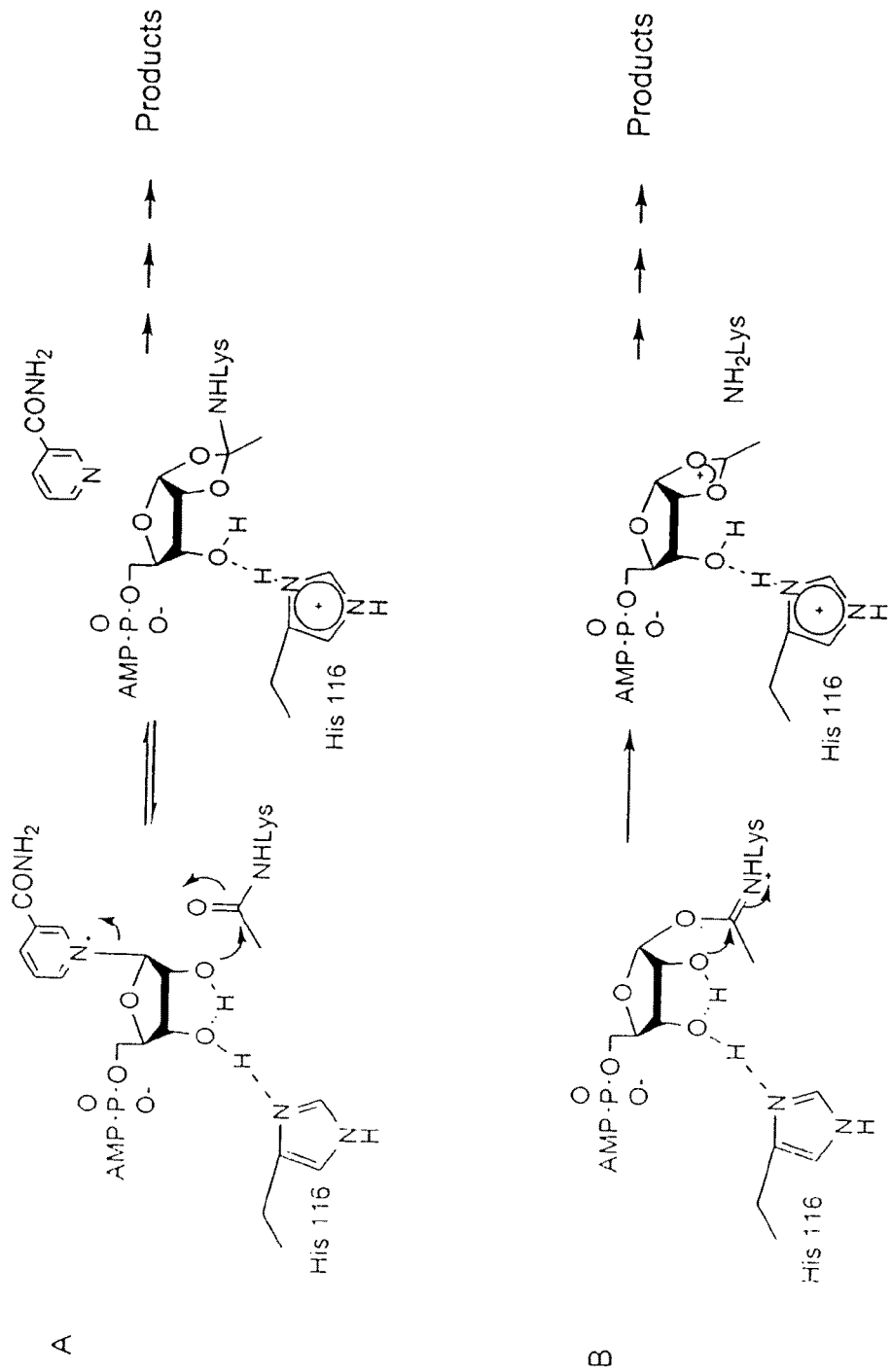

FIG. 7 shows two alternative deacetylation mechanisms proposed for SIR2 (A) Deacetylation mechanism initiated by 2'-OH nucleophilic attack of the amide carbonyl of an acetyl lysine residue. Mechanism A is unlikely because mutation of His to Ala would eliminate nicotinamide exchange. His 116 ligated to 3'-OH acts as a base catalyst to activate 2'-OH through a proton-transfer relay mechanism via 3'-OH. (B) Deacetylation mechanism dependent upon the breakdown of 1'-O-amidate by 2'-OH attack, downstream from nicotinamide bond cleavage. Mechanism B permits nicotinamide exchange prior to 2'-OH activation, consistent with the exchange reported for the His to Ala mutant.

Figure 8:
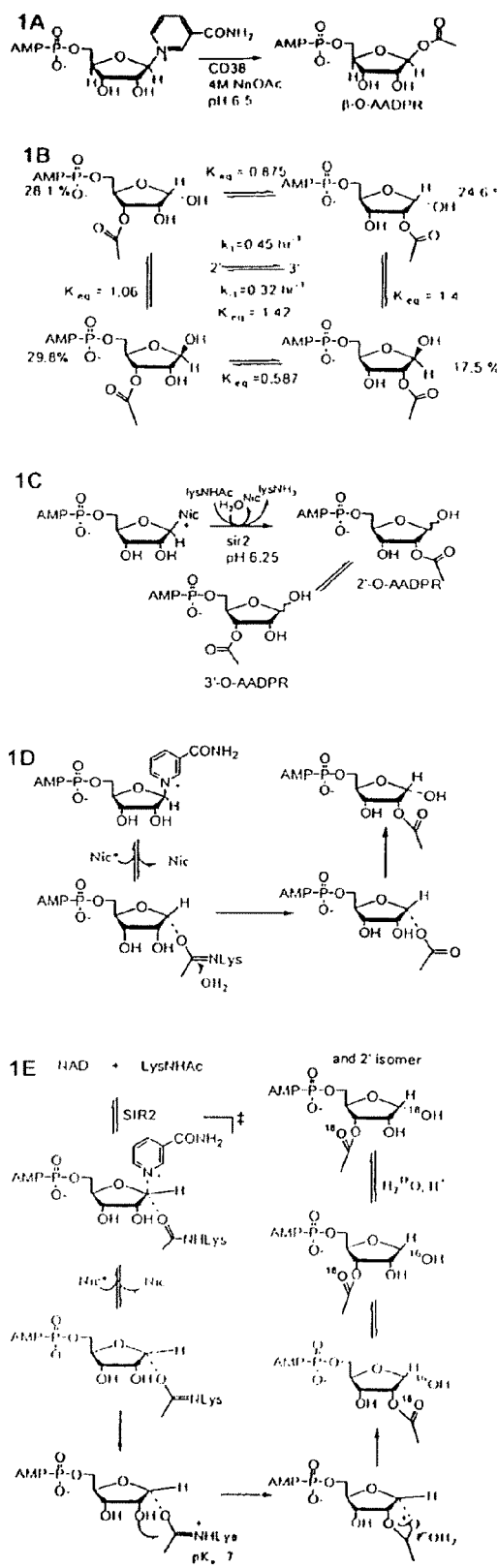

FIG. 8 shows various reaction schemes discussed in the Specification.

Scheme 1A. CD38 catalyzed synthesis of β-1'-AADPR.

Scheme 1B. Observed equilibria of 2'-substituted and 3'-substituted α and β AADPRs and relative equilibrium populations at 15° C.

Scheme 1C. Reaction sequence from NAD$^+$ in Sir2p catalyzed deacetylations.

Scheme 1D. ADP-ribosylation dependent deacetylation generating a-1'-AADPR with migration to 2'-AADPR.

Scheme 1E. ADP-ribosylation dependent Sir2p catalyzed deacetylation mechanism generating 2'-AADPR, 3'-AADPR and $^{18}$O labeled products.

Figure 9:
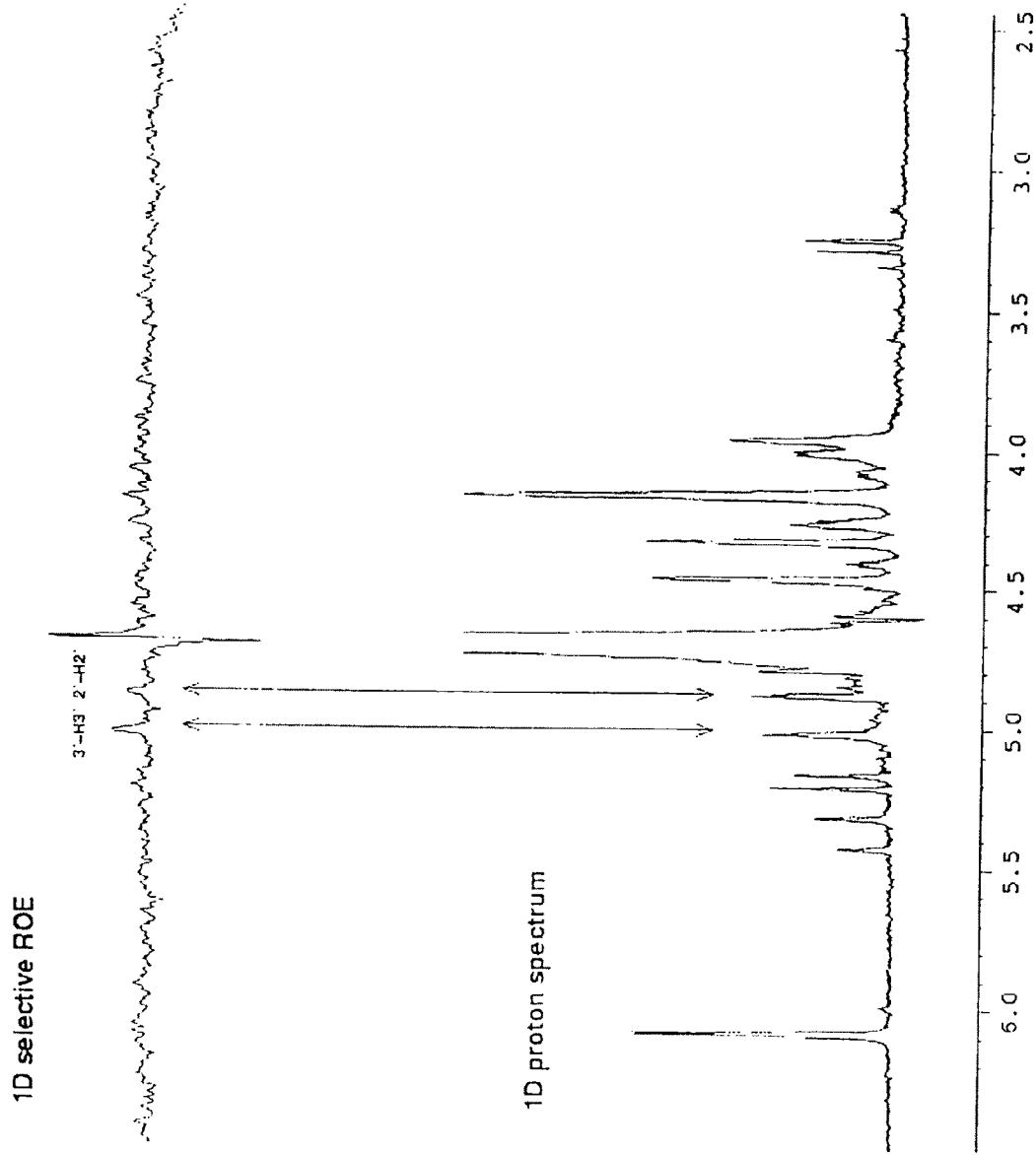

FIG. 9 shows an NMR trace of 2'/3'-O-AADPR.

Figure 10:
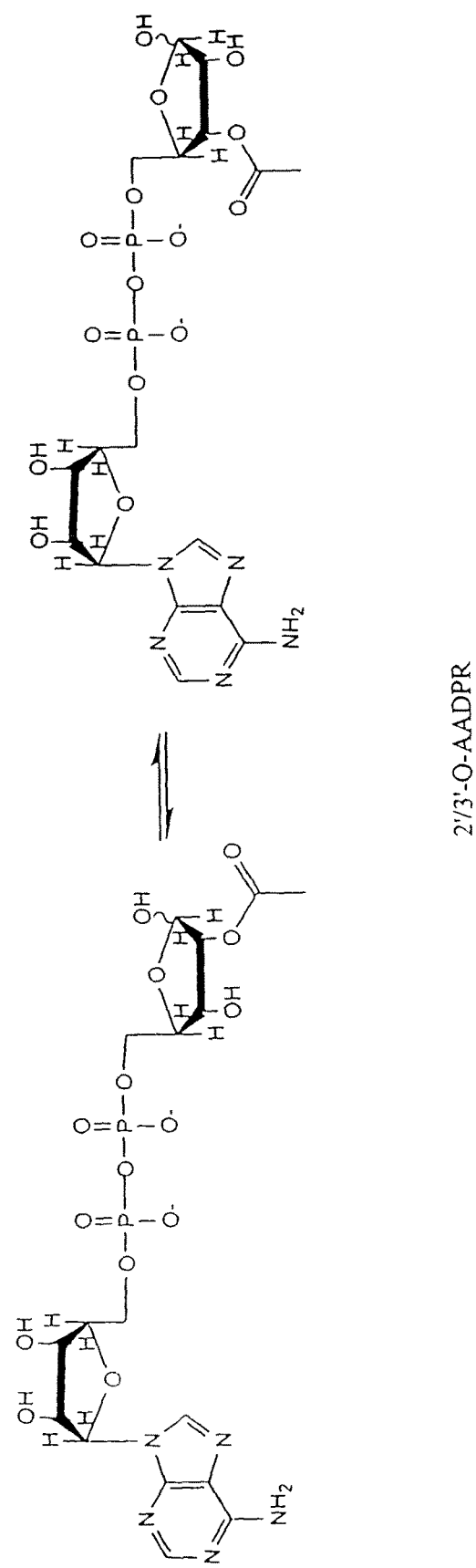

FIG. 10 shows the structure of 2'/3'-O-AADPR.

Figure 11:
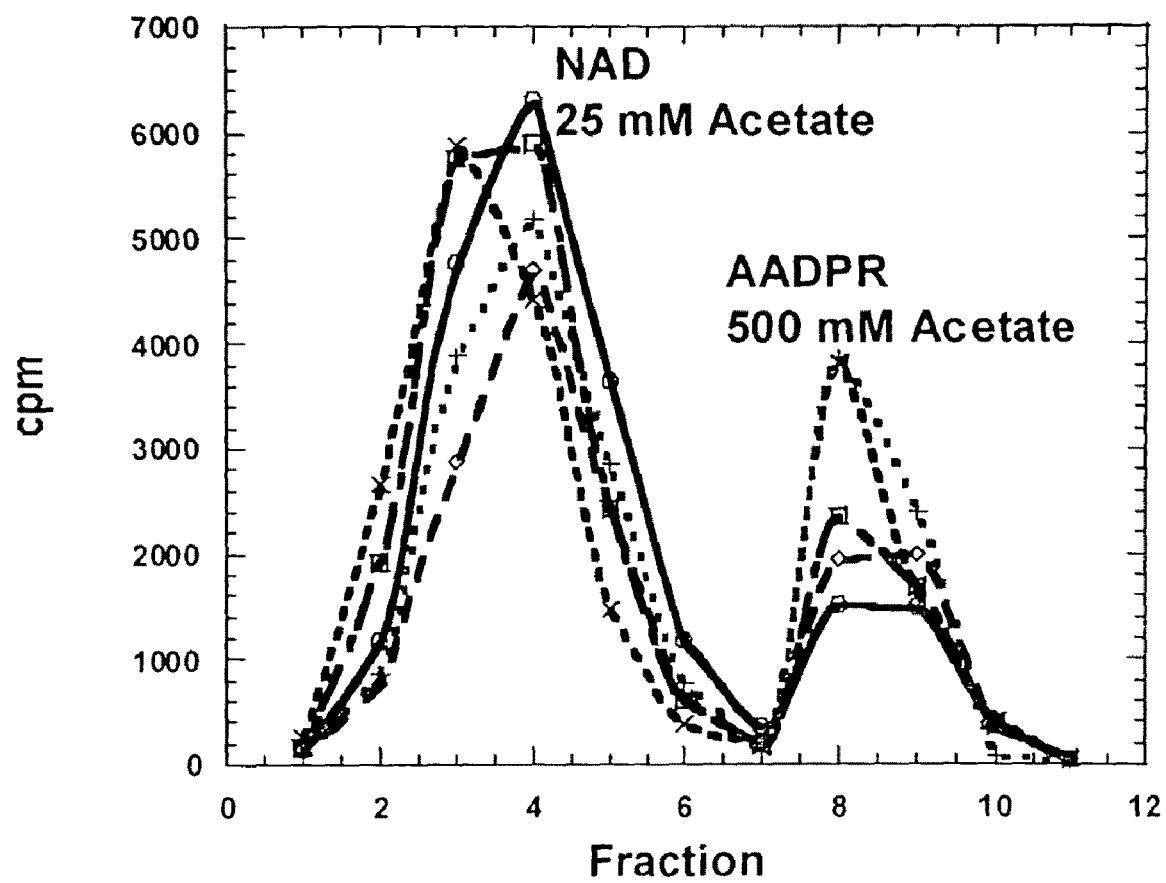

FIG. 11 shows the separation of NAD$^+$ and AADPR to measure Sir2 activity in different time incubations of Sir2 with NAD$^+$ and peptide JB12. Minimum incubation time is 30 minutes.

Figure 12:
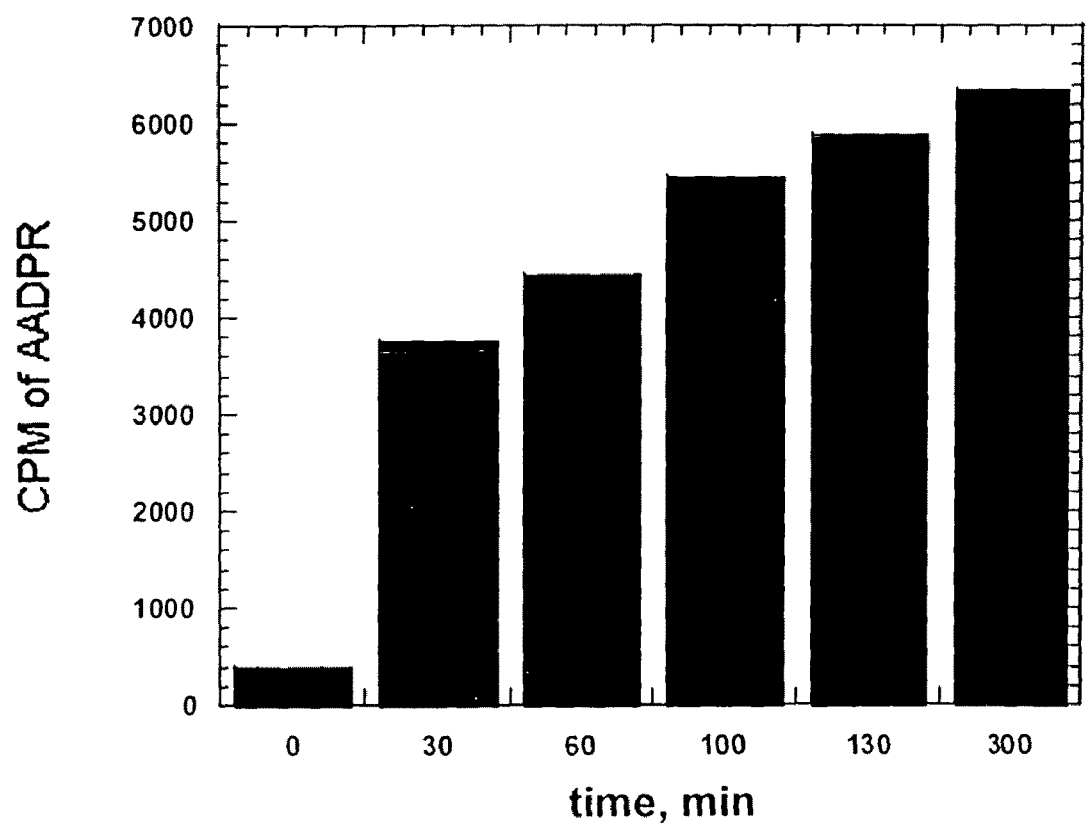

FIG. 12 is a graph showing Sir2 mediated AADPR production versus time as measured by column-isolated AADPR and radioactivity assay.

Figure 13:
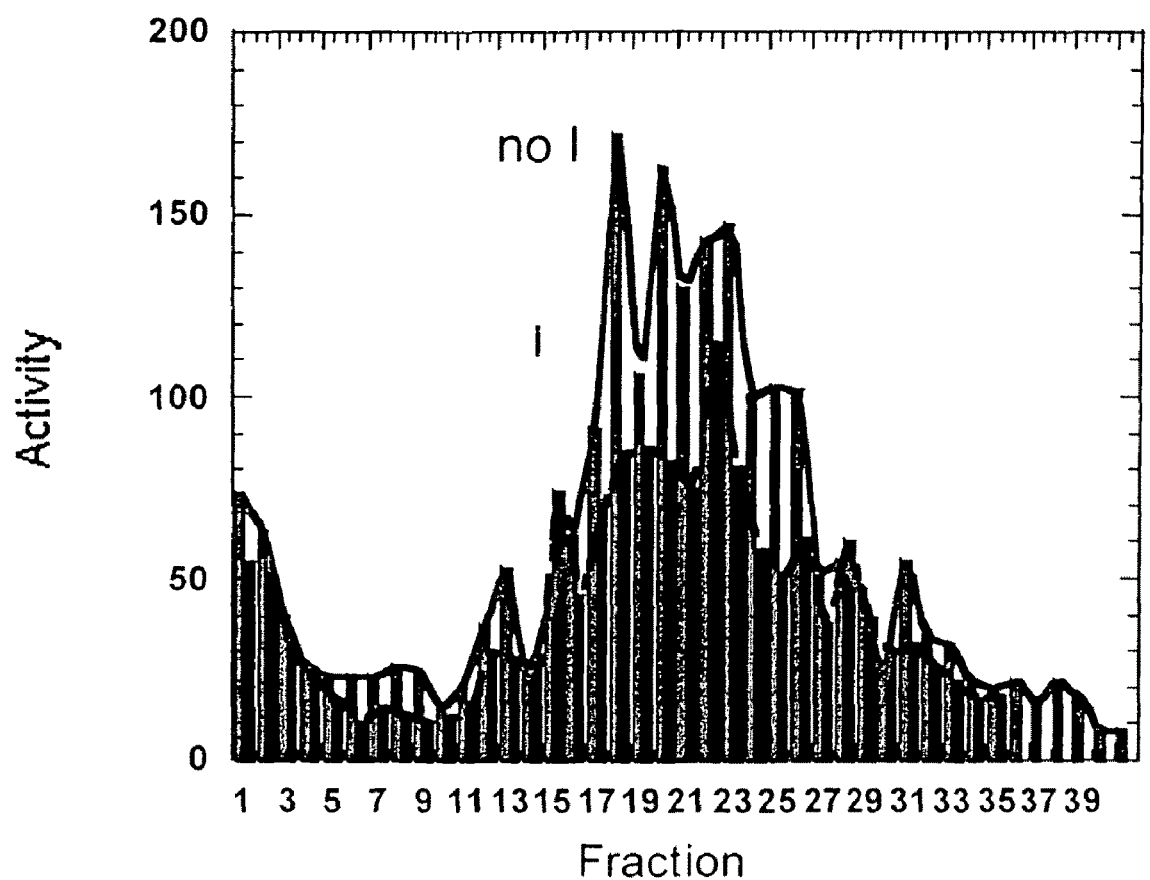

FIG. 13 is a graph showing para-nitrophenyl acetate measured esterase activity in a DEAE-separated liver extract (no I), compared to para-nitrophenyl acetate measured esterase activity in the presence of mM concentrations of all AADPR-like Sir2 inhibitor compound (I).

DETAILED DESCRIPTION OF THE INVENTION

As used herein, "AADPR" means acetyl adenosine diphosphate ribose. 1'-, 2', and 3'-AADPR means the 1'-O, 2'-O and 3'-O regioisomers, respectively, of AADPR. "2'/3'-AADPR" or "2'/3'—O-AADPR" means a mixture of the 2'-AADPR and 3'-AADPR (FIG. 10). "ADPR" means adenosine diphosphate ribose.

As used herein, "Sir2" means silent information regulator 2, or any of its orthologs or paralogs, now known or later discovered, as would be understood by the skilled artisan.

As used herein, "HPLC" means high performance liquid chromatorgraphy; "NMR" means nuclear magnetic resonance; and "MS" means mass spectroscopy or mass spectrometer.

As used herein, "transfection" is the process of inserting DNA into a cell such that genes encoded by the DNA are capable of being expressed by the cell. The DNA can be transiently expressed or stably expressed in the cell.

As used herein, a "peptide" is a sequence of at least two amino acids. Peptides can consist of short as well as long amino acid sequences, including proteins.

As used herein, "NAD+" means nicotinamide adenine dinucleotide.

The present invention is based on two discoveries. The first discovery is the determination that a product of the reaction of a Sir2 with an acetylated peptide and NAD$^+$ is 2'-O-acetyl-ADP-ribose. The 2' acetyl group can transfer to the 3' hydroxyl until an equilibrium is formed between the 2' and 3' forms. Thus, the Sir2 reaction ultimately causes the production of 2'/3'-O-acetyl-ADP-ribose ("2'/3'-AADPR"—FIG. 10). This is contrary to the previously held belief that the product of the reaction is β-1'-AADPR[15,16]. The 2'/3'-AADPR has not been previously described. Because Sir2 uses metabolically valuable NAD to produce 2'/3'-AADPR, and because the product 2'/3'-AADPR is metabolically unstable, the skilled artisan would understand that the product is likely useful as initiators of signaling pathways. The 2'/3-AADPR product is also useful for, inter alia, testing for inhibitors of Sir2 enzymes, for determining and quantifying Sir2 activity in a composition, and for inhibiting Sir2 enzymes. These uses for 2'/3'-AADPR are further described below.

The second discovery that leads to the present invention is that Sir2 enzymes deacetylate peptides other than histones. Examples of such peptides are acetylated p53 and fragments thereof. Based on experimental results described in the Example, the skilled artisan would expect that Sir2 enzymes deacetylate any acetylated peptide of at least two amino acids, wherein at least one of the amino acids comprises a lysine residue that is acetylated at the ε-amino moiety. This finding would lead the skilled artisan to believe that Sir2 enzymes have a much broader role in regulating transcription than was previously appreciated, since it is now understood that Sir2 enzymes can deacetylate any acetylated protein.

Accordingly, the present invention is directed to a purified preparation of 2'/3'-O-acetyl-ADP-ribose. As used herein, "purified" means occupying a greater proportion of a composition than would be found in nature. Preferably, the purified preparation is an aqueous composition having a solute (excluding salts) that is at least 50% 2'/3'-AADPR. More preferably, the purified preparation is at least 75% 2'/3'-AADPR. In even more preferred embodiments, the purified preparation is at least 90% 2'/3'-AADPR. The purity of the preparation can be determined by any means known in the art. A preferred method for determining the purity of 2'/3'-AADPR is by HPLC, e.g., by methods described in the Example below.

In a living cell or a cellular or tissue extract, the 2'/3'-AADPR is generally very short-lived, unless the action of endogenous esterases are arrested. This ephemeral quality of 2'/3'-AADPR can be circumvented by using analogs of 2'-AADPR or 3'-AADPR that are designed to have increased stability from esterase action through the use of well-known substitutes for ester oxygen atoms that are subject to esterase attack. The esterase-labile oxygen atoms in 2'-AADPR and 3'-AADPR would be understood to be the ester oxygen linking the acetate group with the ribose, and the ester oxygen between the two phosphorus atoms. As is known in the art, substitution of either or both of these ester oxygen atoms with a $CF_2$, a NH, or a S would be expected to provide a 2'-AADPR or 3'-AADPR analog that is substantially more stable due to increased resistance to esterase action.

Thus, in some embodiments, the invention is directed to analogs 2'-O-acetyl-ADP-ribose or 3'-O-acetyl-ADP-ribose exhibiting increased stability in cells. The preferred analogs comprise a $CF_2$, a NH, or a S instead of the acetyl ester oxygen or the oxygen between two phosphorus atoms. The most preferred substitute is $CF_2$. Replacement of the acetyl ester oxygen is particularly preferred. In other preferred embodiments, both the ester oxygen and the oxygen between the two phosphorus atoms are independently substituted with a $CF_2$, a NH, or a S.

The 2'/3'-O-acetyl-ADP-ribose product can be prepared by any of a number of chemical or enzymatic methods in the art. Preferably, the 2'/3'-O-acetyl-ADP-ribose is prepared using a Sir2 enzyme, by combining the Sir2 enzyme with $NAD^+$ and an acetylated peptide substrate of the Sir2 in a reaction mixture under conditions and for a time sufficient to deacetylate the peptide. The 2'/3'-O-acetyl-ADP-ribose can be identified and purified from the reaction mixture. Preferably, the 2'/3'-O-acetyl-ADP-ribose is purified chromatographically, for example by HPLC. In some embodiments, the isolation and/or quantitation of 2'/3'-O-acetyl-ADP-ribose can be advantageously simplified by using radiolabeled $NAD^+$ such that the 2'/3'-O-acetyl-ADP-ribose is radiolabeled after the peptide is deacetylated. See, e.g., Example 2 for a non-limiting example of those methods. Alternatively, the skilled artisan would understand that a radioactive acetate-labeled acetylated peptide would also label 2'/3'-O-acetyl-ADP-ribose. The labeled 2'/3'-O-acetyl-ADP-ribose allows for simpler separation methods, where the labeled 2'/3'-O-acetyl-ADP-ribose need only be separated from the radiolabeled $NAD^+$ or acetylated peptide substrate, e.g., with a Sephadex-DEAE column (see, e.g., Example 2 and FIG. 11). Once separated from the radiolabeled substrate(s), radiolabeled 2'/3'-O-acetyl-ADP-ribose can be easily quantified, e.g., by scintillation, which is useful for methods described below where quantitation of Sir2, or determination of inhibitor activity, is desired.

As previously discussed, it is believed that any acetylated peptide of at least two amino acids can usefully serve as a substrate for Sir2, provided at least one of the amino acids is a lysine residue that is acetylated at the ε-amino moiety. The acetylated peptide can comprise any number of amino acids, including three, five, ten, fifteen, eighteen, or more amino acid residues. As is known, there is no particular sequence that is preferred, although most deacetylation occurs in a pair of basic amino acids. See, e.g., ref. 10 and Example 1.

In preferred embodiments, the acetylated peptide substrate is homologous to an acetylated region of the regulatory domain of a p53, for example peptide JB11 or JB12, described in the Example. An acetylated p53 is also a useful substrate for Sir2.

In other embodiments, the acetylated peptide substrate is homologous to an acetylated region of a histone, or an acetylated histone itself.

The described enzyme reaction is expected to be for any Sir2 enzyme, with the exception of Sir2Af1 (see Example). Well-known Sir2 enzymes that would catalyze the described reaction includes, inter alia, Sir2Af2, human Sir2A, yeast Sir2p, Sir2™ from *Thermotoga maritima*, and cobB, from *Salmonella typhimurium*. Useful enzymes include those derived from prokaryotes, including archaeal bacteria and eubacteria, and those derived from prokaryotes, including yeast and humans.

As used herein, the term "derived from", when referring to a Sir2 enzyme, means either (a) extracted from the organism that naturally produces the enzyme, or (b) translated, in vitro or in vivo, from a gene encoding the Sir2 enzyme from the organism. This includes genes transfected into heterologous organisms, e.g., a Sir2 gene derived from a human, translated from the human Sir2 gene transfected into *E. coli*, yeast, a mammalian cell, or an intact mammal.

In additional embodiments, the present invention is directed to methods for determining whether a test compound is an inhibitor of a Sir2 enzyme. The methods comprise the following steps:

combining the test compound with the Sir2 enzyme, $NAD^+$ and an acetylated peptide substrate of Sir2 in a reaction mixture under conditions and for a time sufficient to deacetylate the peptide in the absence of the test compound;

quantifying 2'/3'-O-acetyl-ADP-ribose produced from the acetylated peptide; then comparing the quantity of 2'/3'-O-acetyl-ADP-ribose produced with a quantity of 2'/3'-O-acetyl-ADP-ribose produced under the same conditions but without the test compound. In these methods, the presence of less 2'-O-acetyl-ADP-ribose and/or 3'-O-acetyl-ADP-ribose with the test compound than without the test compound indicates that the test compound is an inhibitor of the Sir2 enzyme.

These methods are useful for evaluating potential inhibitors with any Sir2 enzyme that normally produces 2'/3'-O-acetyl-ADP-ribose. Peptides useful for these reactions include any of the Sir2 peptide substrates previously described. As previously discussed, using a radiolabeled Sir2 substrate can simplify these methods.

In related embodiments, the invention is directed to methods of inhibiting Sir2 enzymes. The methods comprise combining the Sir2 enzyme with an inhibitor found by the method described directly above. In these methods, any Sir2 enzyme that normally produces 2'/3'-O-acetyl-ADP-ribose is a useful target. The Sir2 enzyme to be inhibited can be within a living cell, wherein the inhibitor is inserted into the cell by any of a number of methods, depending on the chemical characteristics of the inhibitor, as is know in the art. For example, the living cell can be a bacterial cell or eukaryotic cell, such as a yeast or a mammalian cell, including a human cell. The mammalian cell can be within a living mammal. In some useful embodiments, the mammal is at risk for, or suffering from, cancer induced by lack of p53-DNA binding. In those embodiments, the Sir2 inhibitor would be expected to prevent Sir2 from deacetylating p53, thus increasing p53 DNA binding.

The present invention is also directed to methods of detecting activity of a Sir2 in a composition. The methods comprise the following steps:

combining the composition with $NAD^+$ and an acetylated peptide substrate of a Sir2 under conditions and for a time sufficient to deacetylate the peptide in the presence of Sir2 activity; then measuring 2'/3'-O-acetyl-ADP-ribose. In these embodiments, the presence of 2'/3'-O-acetyl-ADP-ribose indicates the presence of Sir2 activity in the composition. These methods can be used with any acetylated peptide substrates, including radiolabeled substrates, previously described.

Additional embodiments of the invention are directed to methods of deacetylating an acetylated peptide. The methods comprise combining the peptide with a Sir2 enzyme. In novel aspects of these embodiments, the acetylated peptide is not a histone. As with previously described methods, any Sir2 enzyme that produces 2'/3'-O-acetyl-ADP-ribose is useful for these methods; the methods would also be expected to be useful for the deacetylation of any acetylated peptide that consists of at least two amino acids, wherein at least one of the amino acids comprises a lysine residue that is acetylated at the ε-amino moiety.

The invention is also directed to methods of inhibiting the deacetylation of an acetylated peptide. The methods comprise mixing the acetylated peptide with a Sir2 inhibitor determined by the methods previously described. These methods are useful for inhibiting deacetylation of any acetylated peptide in vitro or in vivo. For example, the acetylated peptide can be in a living cell, e.g., a mammalian cell, which can optionally be a cell in a living mammal, such as a human. A useful embodiment is inhibiting deacetylation of p53 in a mammal at risk for, or suffering from, cancer induced by lack of p53-DNA binding.

As is well known, products of enzyme reactions are generally inhibitors of the same enzyme. Such is also known to be true with Sir2, where nicotinamide inhibits the enzyme[46]. We have also shown that ADPR is a potent inhibitor of AfSir2 (see Example 1). Thus, it would also be expected that 2'/3'-O-acetyl-ADP-ribose would inhibit Sir2. Accordingly, the present invention is directed to methods of inhibiting the Sir2-directed deacetylation of an acetylated peptide. The methods comprise mixing the acetylated peptide with 2'/3'-O-acetyl-ADP-ribose or any of the analogs of 2'/3'-O-acetyl-ADP-ribose previously described. Preferred peptides for these methods include histones and p53. Although these methods are useful in vitro, in preferred embodiments the acetylated peptide is in a living cell. The living cell can be a prokaryotic cell or, preferably, a eukaryotic cell. The eukaryotic cell can be a mammalian cell, optionally in a living mammal, such as a human. Usefully, the mammal is at risk for, or suffering from, cancer induced by lack of p53-DNA binding.

Additionally, the invention is directed to prodrugs of 2'/3'-O-acetyl-ADP-ribose. The prodrugs comprise 2'/3'-O-acetyl-ADP-ribose covalently bonded to a moiety by an esterase-sensitive bond. In these embodiments, the prodrug is capable of passing into a cell more easily than 2'/3'-O-acetyl-ADP-ribose. Many methods for making such prodrugs are known. One example is methods using salicylate as a moiety, e.g., using methods described in Khamnei & Torrence[47].

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

Example 1

Studies Relating to Products, Mechanisms, and Substrates of Sir2

Methods

Enzyme purifications and assays. Sir2 enzymes were purified as GST fusions except for Sir2Af1 and Af2 which were purified as native enzymes[19]. Assays for activity on [$^3$H]-acetylated chicken histones were carried out as described[19]. Peptides were synthesized by the Johns Hopkins Medical Institutions Sequencing and Synthesis Facility and purified by HPLC on an RP-18 column before use. Peptides JB11 and JB12 were assayed for deacetylation as follows. Peptide JB12D (deacetyl version) was made as a standard and comigrated with the JB12 product peak on HPLC. For peptides JB11 and JB12, 100 µg of peptide was incubated with 10 µg of GST-Sir2p and 200 mM NAD overnight at 30° C. in 50 mM Tris-Cl pH 8.0, 50 mM NaCl. Reaction products were separated on Star chromatography workstation with a C-18 analytical column and a 0-100% gradient of acetonitrile. The flow rate was 0.4 ml/min; absorption was monitored at 210 nm. The same reaction conditions were used for Af2Sir2, TmSir2 and GST-Sir2A except incubation was performed at 55° C. for Af2Sir2 and TmSir2 and at 37° C. for GST-Sir2A. HPLC fractions (500 µl) collected after HPLC separation were analyzed by MALDI-TOF spectrometry on an Applied Biosystems Voyager DE-STR instrument.

Purification of GST-p300 and reactions with p53. GST-p300 was purified from plasmid pGEX-2T-p300[29], the kind gift of Shelley Berger. Bacterial cells containing expression vector were induced with 300 µM IPTG $OD_{600}=0.6$ and grown at 30° C. for 6 µl. Cells were collected and protein purified using glutathione-Sepharose4B beads (Amersham-Pharmacia) according to the manufacturer's instructions.

Acetyl-p53 was prepared from yeast strain YPH-500 transformed with expression vector pRB16 containing p53 cDNA and cell extracts prepared[1,12]. Extract containing 4.6 mg of protein was incubated with 12 µg of anti-p53 antibody DO-1 conjugated to agarose (Santa Cruz Biotechnology) for 1 hour at 4° C. The beads were washed and incubated with 5 µg of GST-CBP and 37.5 ml of [$^3$H]-acetyl-CoA (3.7 Ci/mmol, 67 µM, Amersham-Pharmacia) in HAT buffer (50 mM Tris-Cl pH 8.0, 10% glycerol, 0.1 mM EDTA, 1 mM DTT, 50 mM NaCl and 4 mM sodium-butyrate) for 1 hour at 30° C. Following acetylation, beads were washed and divided into four tubes. each containing 10 µl, and incubated for 3 hours with 5 µg of GST-Sir2A (37° C.), GST-Sir2 (30° C.) and Af2Sir2 (55° C.), 200 µM NAD, 50 mM Tris-Cl pH 8.0 and 50 mM NaCl in a final volume of 30 µl. The control reaction was without enzyme at 37° C. Following deacetylation, beads were washed, and protein released by addition of SDS sample buffer and boiling. The samples were separated on 10% SDS-PAGE. After electrophoresis, the samples were transferred to a PVDF membrane and immunoblotting was performed using 06-758 antibody (Upstate Biotechnology) or DO-1 according to the manufacturers' instructions.

Methods of Analysis. Reagents and buffers were obtained from commercial ventors. HPLC separations of NAD and its products were run in a Waters 600 pump/controller, fitted with a Waters 2487 dual wavelength UV/Vis detector or a Waters 996 PDA multi-wavelength detector instrument. HPLC chromatograms were collected with a 260 nm absorbance unless otherwise indicated. Kinetic studies via HPLC were performed using a programmable Waters 717 autosampler with temperature control. $^1$H NMR studies were performed on 300 MHz or 600 MHz Bruker spectrometers with computerized temperature control. The MS and MS/MS experiments were conducted using either a Perseptive Mariner ESI-TOF coupled to a capillary MicroTech C-18 column, or a Finnigan LCQ instrument.

Synthesis of β-1'-AADPR. CD38 was expressed and purified as reported[43]. 100 mg of NAD was dissolved in 5 mL, 4 M NaOAc pH 6.5. To this solution was added 50 µg CD38 enzyme dissolved in 50 mM NaOAc pH 5.0. After overnight incubation at 37° C. the material was filtered (Millipore Biomax 10K NMWL centrifugal filter device), injected onto a Waters C-18 preparative column of dimensions 19 mm×300 mm, and eluted with 0.5% TFA at a flow-rate of 4 mL/min. A peak eluting before NAD$^+$ (40 min versus 50 min respectively) was collected and lyophilized. The product (yield-28%) was characterized by MS and NMR and determined to be β-1'-AADPR. Data: $^1$H NMR D$_2$O d (8.61, s, 1H), (8.38, s, 1H), (6.14, d, 1H), (5.86 s, 1H), (4.5, m, 1H), (4.35, m, 1H), (4.18-4.00, m, 6H), (2.02, s, 3H). MS (negative ion) 600 amu. MS/MS (600): 540, 352 and 333 amu.

Purification of 3'-AADPR and NMR characterization Sir2Af2 products for NMR analysis were obtained by incubation (40° C. overnight) of 300 µg Sir2Af2 enzyme, 20 mg NAD$^+$, and 70 mg JB12 peptide in 5 mL 40 mM potassium phosphate buffer pH 6.25. The reaction was quenched by filtration through a 10,000 MW cutoff membrane (Millipore Biomax 10K NMWL centrifugal filter device). Fractions of the filtrate (1 mL) were loaded onto DEAE A-50 columns (1 mL) pre-equilibrated with 25 mM NaOAc pH 6.0. Elution with 2 mL of 25 mM NaOAc pH 6.0, 3 mL 100 mM NaOAc pH 6.0 and 2 mL 1M NaOAc pH 6.0 gave fractionation of products. The last three 1 mL fractions contained 60%-100% of the acetyl-O-ADP-ribose, as shown by MS and HPLC. Separation of 2'-AADPR and 3'-AADPR was accomplished using a semi-preparative C-18 column eluted with 1 mM potassium phosphate (pH 5.0) at a flow rate of 2 mL/min (5 mL injection volume). The largest peak (3'-AADPR) eluted at 14 min and was roto-evaporated to dryness at 2° C. in less than 30 min under high vacuum. An HPLC chromatogram of this material (50 mM ammonium acetate eluant with a semi-preparative C-18 column of dimensions 7.8 mm×300 mm) indicated it was 95% pure. This material was kept ice-chilled in $D_2O$ and $^1H$ NMRs were taken with probe temperatures varying from 0 to 25° C. 1D and 2D COESY and NOESY experiments were performed to provide unequivocal assignment of 3'-AADPR, and the time-dependent conversion of this material to the 2' isomer was observed. 3'-AADPR $^1H$ NMR, $D_2O$, δ (8.52, s, 1H), (8.22, s, 1H), (6.09, d, 1H), (5.32, d, 1H beta isomer) (5.17, d, 1H alpha isomer), (5.02, m, 1H), (4.7, m, 1H), (4.45, m, 1H), (4.32, m, 1H), (4.23, m, 1H), (4.14, m, 2H), (4.126, m, 1H), (3.95, m, 2H), (2.05, s, 3H). NOEs (2.05, 5.02), COESY cross peaks (5.02, 4.23), (5.32, 4.23), (5.17, 4.23). MS (negative ion mode): 600, 540 and 346 amu.

Purification of 2'-AADPR and NMR characterization. The 2'-AADPR isomer eluted as the second peak in the HPLC chromatogram described above. HPLC (50 mM ammonium acetate pH 5.0) showed that 2'-AADPR converts readily to the 3'-AADPR. The 2'-AADPR was characterized by allowing the 3'-AADPR to reach equilibrium with it, at a 47:67 ratio (2'-AADPR:3'-AADPR) as determined by integrations of HPLC peaks. The COESY and NOESY cross peaks and the $^1H$ NMR data allowed full characterization: 2'-AADPR. $^1H$ NMR, $D_2O$, δ (8.52, s, 1H), (8.22, s, 1H), (6.09, d, 1H), (5.39, d, 1H beta isomer) (5.20, s, 1H alpha isomer), (4.87, m, 1H), (4.7, m, 1H), (4.45, m, 1H), (4.32, m, 1H), (4.23, m, 1H), (4.14, m, 2H), (4.126, m, 1H), (3.95, m, 2H), (2.12, d, 3H). NOEs (2.12, 4.87), COESY cross peaks (4.02, 4.87), (5.39, 4.87), (5.20, 4.87). MS (negative ion mode): 600, 540, 346.

Interconversion rates of 2'- and 3'-AADPR. Sample of both 2'- and 3'-AADPR were incubated at 15° C. and analyzed by HPLC at 40 min intervals (C-18 column; 50 mM ammonium acetate pH 5.0). The percent of the 3'-isomer at a given time was fit to the equation 3'-AADPR (%)=$P_a$ exp (-kt)+$P_f$ where $P_a$+$P_f$=$P_0$; where $P_a$ is the percent of the 3'-isomer above equilibrium at time=0, t is time and k is the first order rate constant for the conversion. $P_f$ is the percent at equilibrium and $P_0$ is the initial percent. HPLC and NMR analysis established the 2'- and 3'-isomers concentration as a function of time. NMR was in 10% $d_4$-methanol/90% $D_2O$ at 0° C. or in 100% $D_2O$ at 20° C.

Low temperature studies of Sir2Af2 to identify order of product production. Sir2Af2 catalyzed deacetylation reactions were performed at 8° C. to determine the order of product formation. A 200 μL solution containing 150 μM NAD$^+$, 300 μM peptide JB12, in 40 mM potassium phosphate pH 6.2 were cooled to 8° C. and then 1 μL of 9 μg/μL of Sir2Af2 was added to initiate the reaction. Reactions were assayed by HPLC using 0.5% TFA as an eluant. Peals at 17 and 20 min were used to quantitate 3'- and 2'-AADPR at 30 minute intervals.

Low temperature $^1H$ NMR analysis of Sir2p reaction products. A solution of 1.7 mg Sir2Af2 enzyme in 95% $D_2O$, 50 mM potassium phosphate pH 6.3 was concentrated to 550 μL using centrifugation filtration. This sample was mixed with 2 mg JB12 peptide and cooled to 5° C. in a 600 MHz NMR spectrometer. Spectra were obtained and 280 μL of ice-chilled 22 mM NAD$^+$ solution in 50 mM potassium phosphate pH 6.3 in 99% $D_2O$ was added to initiate the reaction. $^1H$ NMR 1D spectra were obtained at intervals over 18 hr at 5° C.

Elimination of β-1'-AADPR as a Sir2p product. Authentic β-1'-AADPR (100 μM, in 40 mM phosphate buffer at pH 6.25 was incubated for one hr at 55° C., and analyzed by HPLC for production of 2'- or 3'-AADPR isomers. The resulting chromatograms showed no change in the β-1'-AADPR and no production of 2'- or 3'-AADPR as compared to controls.

$H_2^{18}O$ incorporation into 2'- and 3'-AADPR. Reactions containing 2 μg Sir2Af2 in 200 μL $H_2^{18}O$ (94.5%, containing 40 mM potassium phosphate pH 7.0), and 100 μg JB12 peptide and 300 mM NAD$^+$ were incubated at 55° C. and assayed by injection onto a C-18 capillary column in LCMS negative ion mode, with 0.5% formic acid as eluant. Peptide, NAD$^+$, ADPR, and AADPR were well resolved. MS of $^{18}O$ incubations versus $^{16}O$ controls indicated a 2 amu mass increase (602 versus 600) for AADPR, due to a single $^{18}O$ incorporation. MS/MS of both $^{16}O$ and $^{18}O$ samples were identical with a major fragment observed at m/z=540 due to loss of HOOCCH$_3$, and establishing that $^{18}O$ is incorporated into the acetate group. Purification of 2'- and 3'-AADPR from $^{18}O$ reactions established that both incorporate a single $^{18}O$.

Acid-catalyzed $^{18}O$ exchange reactions. Sir2 reactions containing either $H_2^{16}O$ or $H_2^{18}O$ (as above) were quenched with 2 volumes of $H_2^{16}O$ or $H_2^{18}O$ in 10% $d_4$-acetic acid. Analysis by LCMS (as above) and MS/MS (molecular mass and fragmentations) gave: ($^{16}O$, Sir2Af2 reaction, $^{18}O$, H$^+$) M$^-$=602, fragmentation=542; ($^{18}O$, Sir2p reaction $^{18}O$, H$^+$) M$^-$=604, fragmentations=542, 540; ($^{18}O$, Sir2p reaction, $^{16}O$, H$^+$) M$^-$=602, fragmentation=540; ($^{16}O$, Sir2p reaction, $^{16}O$, H$^+$) M$^-$=600, fragmentation=540. An ADPR sample was incubated in the quench medium as a control with results as follows: ($^{16}O$, H$^+$) M$^-$=558; ($^{16}O$, pH 7.5) M$^-$=558; ($^{18}O$, H$^+$) M$^-$=560; ($^{16}O$, pH 7.5) M$^-$=558. Similar results were obtained with yeast Sir2p.

Ara-F-NAD$^+$ as an NAD$^+$ analogue. Ara-F NAD$^+$ is an inhibitor of ADP-ribosyl-transferase and was used to evaluate Sir2Af2. Ara-F-NAD$^+$ was synthesized as previously reported[44]. Deacetylation of peptide JB12 (300 μM) by Sir2Af2 (10 μg) in the presence of ara-F-NAD$^+$ (50 μM) was tested in 200 μL of 40 mM potassium phosphate pH 6.25. No change of ara-F-NAD$^+$ was detected by C-18 reverse phase HPLC. Incubation of ara-F-NAD$^+$ with 5 mM [Carbonyl-$^{14}C$]-nicotinamide (55 mCi/mmol; American radiolabeled chemicals) in the presence of 300 μM peptide and 10 μSir2Af2 (20 μL) followed by HPLC analysis indicated no radioactivity incorporated into ara-F-NAD$^+$. A control run with JB12-[Carbonyl-$^{14}C$]-peptide and NAD$^+$ established [Carbonyl-$^{14}C$]-nicotinamide exchange into NAD$^+$, confirming the Sir2 base-exchange reaction. A second control used the ADP-ribosyl-transferase CD38 as the exchange enzyme, showing full base exchange between [$^{14}C$]nicotinamide and ara-F-NAD$^+$. Inhibition of Sir2Af2 by ara-F-NAD$^+$ was evaluated by incubation of Sir2Af2 enzyme (7 μM) and ara-F-NAD$^+$ (20 μM) in the presence of 300 μM JB12 peptide in potassium phosphate pH 6.25 buffer. A reaction mixture lacking ara-F NAD$^+$ was the control. A positive control used the same reaction components but 500 nM CD38 in the presence of 5 μM ara-F-NAD$^+$. Reactions were initiated after 6 h by adding 150 μM NAD$^+$. Reactions were evaluated for catalytic turnover using HPLC. Catalytic turnover of Sir2Af2 was not inhibited by ara-F-NAD$^+$ under these reaction conditions.

Results

Figure 1:
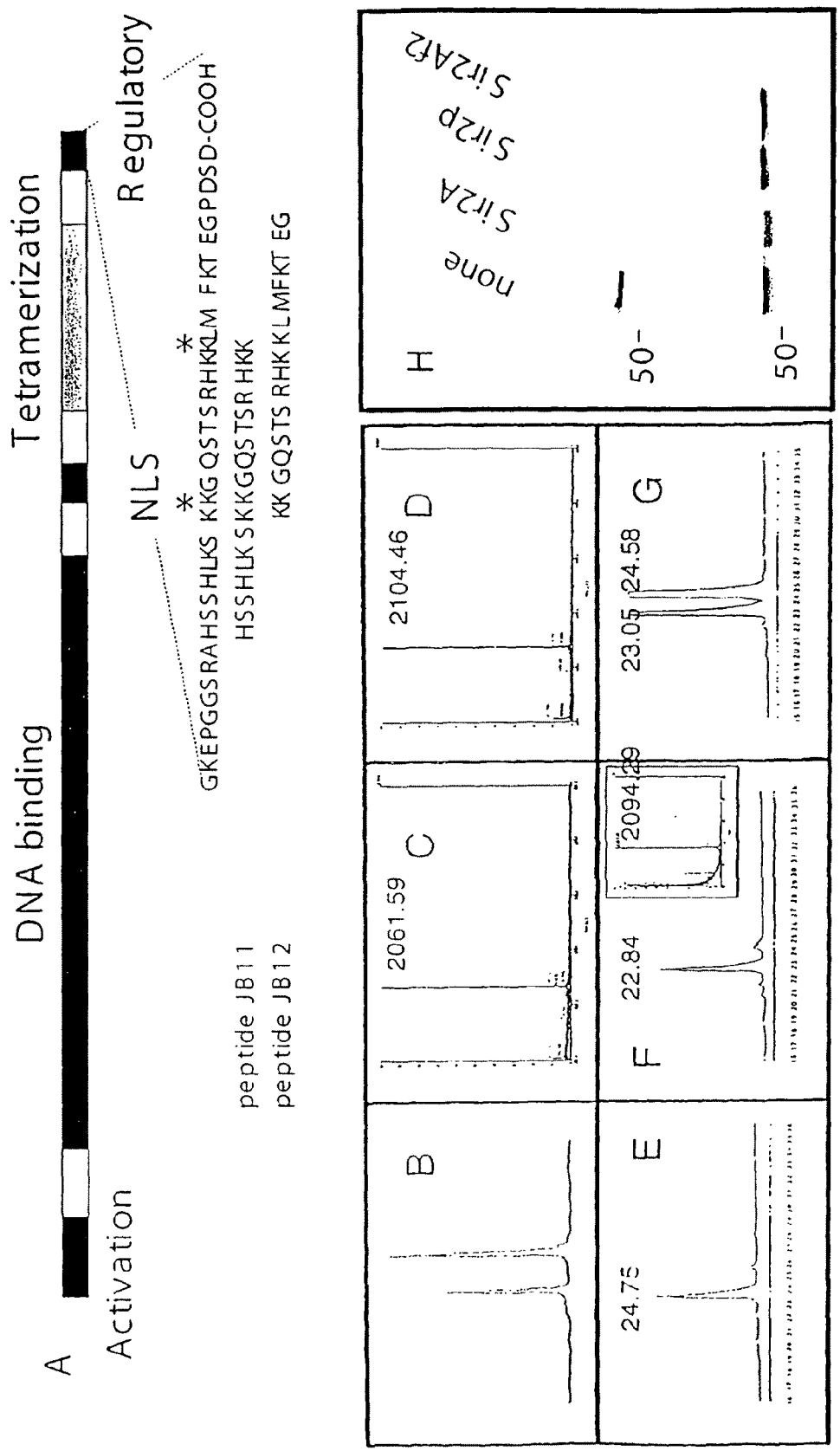
FIG. 1 shows graphics, HPLC traces and immunoblots of p53 and derived peptides are substrates for Sir2p and related proteins. A. Bolded residues are acetyl-lysine in JB11 and 12 and lysine in JB12D. B-G. HPLC separation (numbers are retention times) and MS analysis (numbers are amu) of substrate and product peaks. B. HPLC analysis of JB11 reaction with Sir2p. C, D. MS of two major peaks (product, C; substrate, D) from HPLC in panel B. E. HPLC of peptide JB12. F. HPLC of peptide JB12 following treatment with Sir2p. Inset is MS of major peak. G. HPLC of mixture of peptides JB12 and JB12D. H. p53 activity on full-length p53 expressed in yeast, immunoprecipitated with anti-p53 DO-1 and acetylated in vitro with p300. Upper panel is immunoblotted with anti-acetyl p53 antibody specific to lysines 373 and 382. Lower panel is immunoblotted with antibody FL-393 reactive against acetylated and deacetylated forms of p53.

Acetyl p53 and fragments are substrates of Sir2 deacetylases. Histones are proposed to be a major substrate for Sir2 protein in yeast and other organisms. However, many proteins are acetylated at the ε-amino groups of lysines[24]. A well-characterized example is p53, acetylated on lysines 373 and 382. Synthetic 18-mer peptides, corresponding to p53 fragments acetylated at those positions, were incubated with Sir2 enzymes. All enzymes tested, except Sir2Af1, and including Sir2Af2, human Sir2A and yeast Sir2, deacetylated the peptides acetylated on residue 373 (JB11) and 382 (JB12) (FIG. 1A; Table 1). Further experiments indicated that JB12 was a >4-fold better substrate for Sir2Af2 than JB11 (FIGS. 1B, 1F). As with deacetylation of histones and histone-derived peptides, p53 peptide deacetylation was absolutely dependent on NAD$^+$. Deacetylation was directly confirmed by separation of substrate and product by HPLC over C-18 columns (FIGS. 1B, E-G) and MS determination of masses of substrate and product peaks (FIGS. 1C, D, F inset).

Sir2Af2 and other Sir2-like enzymes were also tested for activity on full-length native acetylated p53. Native acetylated p53 was obtained by acetylating immunoprecipitated p53 in vitro with p300. The immunoprecipitation used monoclonal antibody DO-1, raised against the N-terminus of p53. It precipitates both acetylated and nonacetylated forms of p53. Acetylated p53 was incubated in the presence and absence of Sir2 enzymes (FIG. 1H). The proteins were separated on SDS-PAGE gels and immunoblotted with an antibody specific for p53 acetylated at positions 373 and 382 as well as with FL-393, an antibody that binds to all forms of p53. All three Sir2p enzymes tested deacetylated p53 (FIG. 1H).

TABLE 1

Activity of various Sir2 enzymes on histone and p53 substrates.

| | | Substrate and Products | | | | |
|---|---|---|---|---|---|---|
| Enzyme | Organism | [$^3$H]-histones | p53 (native) | JB11 | JB12 | NAD$^+$ products analyzed$^a$ |
| Sir2p | Saccharomyes cerevisiae | + | + | + | + | + |
| Sir2Af1 | Archaeoglobus fulgidus | − | − | NT$^b$ | − | NT |
| Sir2Af2 | Archaeoglobus fulgidus | + | + | + | + | + |
| Sir2Tm | Thermotoga maritima | + | NT | + | + | + |
| cobB | Salmonella typhimurium | + | NT | + | NT | + |
| Sir2A | Homo sapiens | + | + | + | NT | + |

$^a$AADPR and nicotinamide products were observed by HPLC/MS
$^b$NT, not tested

Activities and reaction products are conserved with several Sir-2-like deacetylases. The p53 deacetylase activity of the Sir2 enzymes tested (yeast Sir2p, Sir2Af1 and 2, Sir2Tm, cobB and human Sir2A) is phylogenetically conserved. The enzymes fall into two classes: (1) the predominant class of proteins active on all physiologic substrates tested (intact histones, native p53, peptides JB11 and JB12), and (2) the exception, Sir2Af1, reportedly active on chemically acetylated p53[18], but inactive on all substrates tested here.

The products of the reactions observed by HPLC include nicotinamide, ADP-ribose and AADPR in reactions catalyzed by purified enzymes from archaeal Sir2Af, human Sir2A, yeast Sir2p, and eubacterial cobB and Sir2Tm proteins. AADPR was formed in all cases, as well as varying amounts of ADP-ribose.

Chemical synthesis of β-1'-AADPR. The AADPR product of the Sir2 reaction has the mass expected for β-1'-AADPR, but the same mass is expected for 2'-AADPR and 3'-AADPR[15,16]. We synthesized authentic β-1'-AADPR by a variation of a previously reported method[25]. The retaining glycohydrolase CD38 formed milligram quantities of the β-1'-AADPR isomer when incubated with millimolar concentrations of NAD$^+$ in saturated (4 M) sodium acetate at pH 6.5 (see Scheme 1A of FIG. 8 for synthesis and structure). HPLC comparison of standard β-1'-AADPR (See NMR in FIG. 2) and AADPR generated by Sir2p showed that the two compounds were differed (retention times 28 and 32 min, respectively). The difference in chemical identity between Sir2p-derived AADPR and β-1'-AADPR was confirmed by MS/MS studies, showing that fragmentation patterns of Sir2p product and β-1'-AADPR differed although their masses were identical (FIG. 3).

Characterization of 2'- and 3'-AADPR from Sir2p reactions. Products of the Sir2p reaction were produced in reactions containing 100 mg JB12 peptide, 30 mg NAD$^+$ and 300 μg enzyme and purified by anion exchange and HPLC chromatography. Samples dissolved in 750 μL volumes of ice-chilled D$_2$O were determined to be approximately 95% pure prior to $^1$H NMR analysis.

Figure 2:
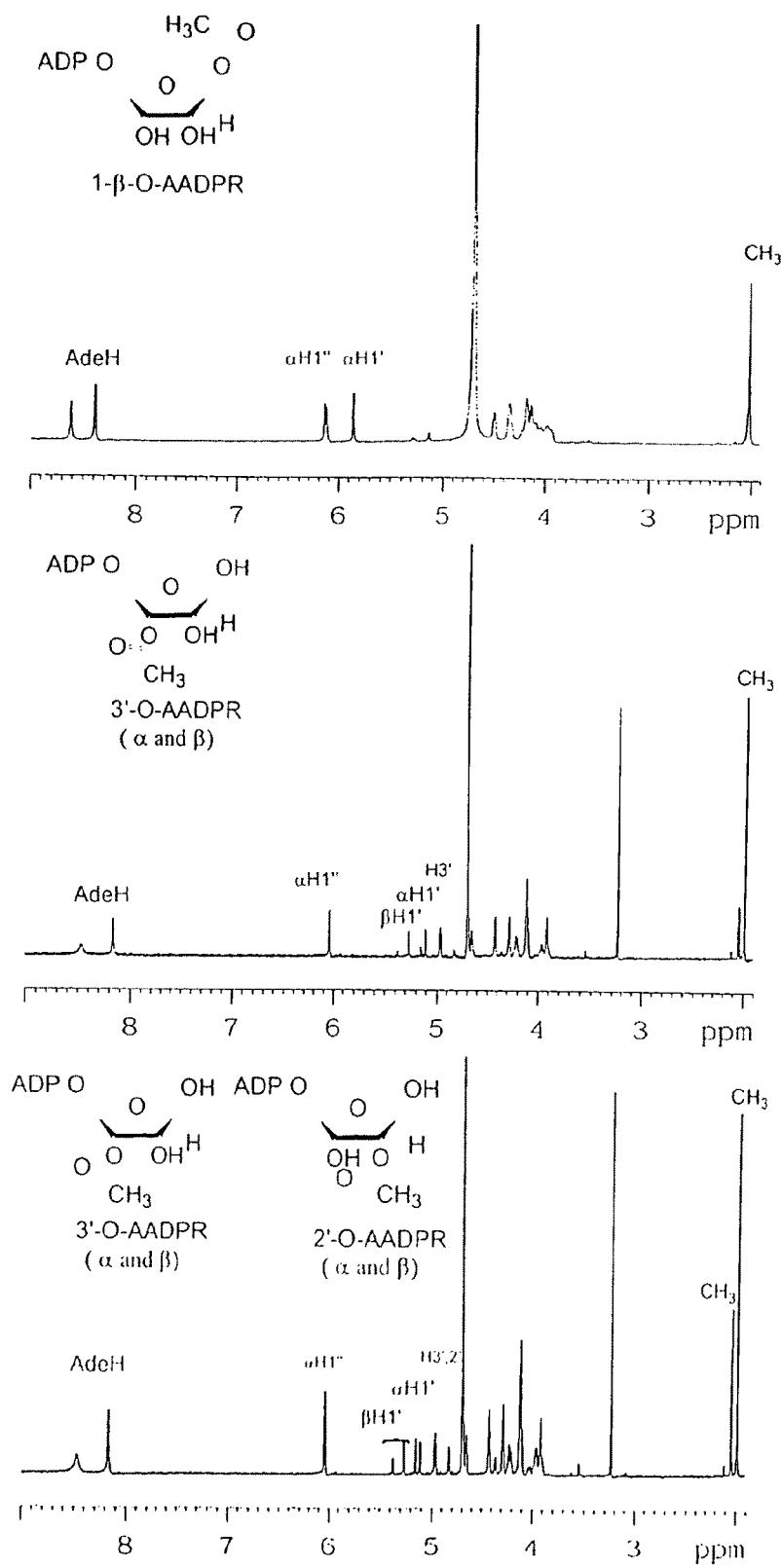
FIG. 2 shows NMR traces of various preparations relating to the structure of the SIR2 product. Top Panel: $^1$H NMR of β-1'-AADPR in $D_2O$ (300 MHz). Middle Panel: $^1$H NMR of 3'-AADPR at 15° C. in $D_2O$ (600 MHz). Bottom Panel: Sample from middle panel aged several h at 20° C. (600 MHz) showing equilibrium of 2'- and 3'-AADPR isomers.
Figure 3:
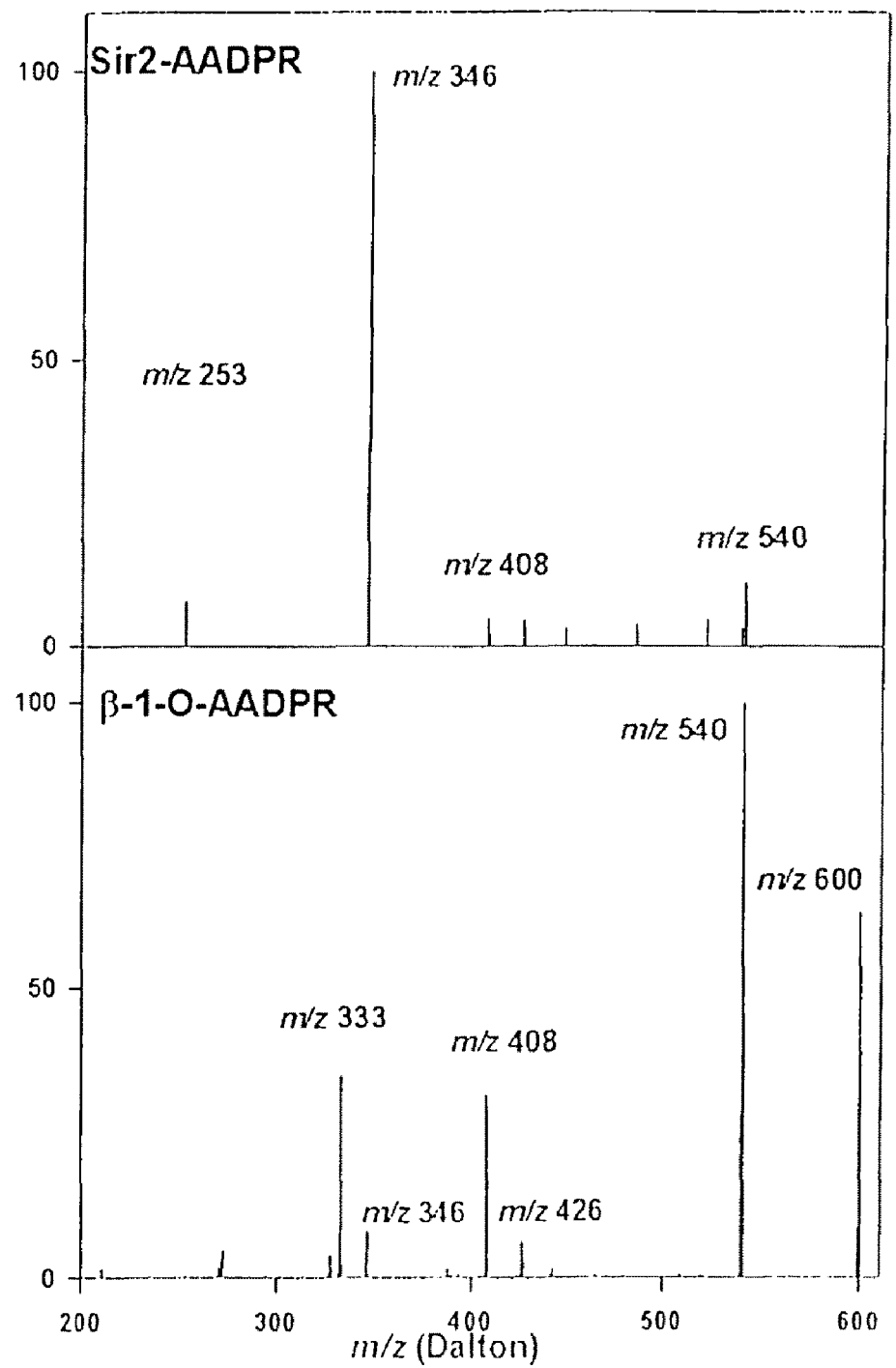
FIG. 3 shows an MS/MS comparison of Sir2p derived AADPR and β-1'-AADPR.

The $^1$H NMR of the Sir2p product (FIG. 2, middle panel) is different from that of β-1'-AADPR, although the acetate moiety is present, based upon the methyl resonance at 2.1 ppm (FIG. 2, top and bottom panels). When this sample was reanalyzed after refrigeration overnight the $^1$H NMR spectrum changed. The minor peaks (FIG. 2, middle panel) became more fully developed (FIG. 2, bottom panel); subsequent spectra indicated that a stable ratio of peaks had been established. HPLC analysis yielded two peaks absorbing at 260 nm. Analysis by MS and MS/MS confirmed that both molecular ions had the predicted AADPR mass of 600 (m/z, negative mode) and both had identical fragmentation patterns (MS/MS), strongly supporting the products as 2'- and 3'-regioisomers of AADPR (see Methods).

Identification of 2'- and 3'-AADPR isomers. We identified the two species as 2'- and 3'-AADPR isomers on the basis of 2D NMR experiments (COESY and NOESY) on freshly purified AADPR performed at 0° C. in 10% d$_4$-methanol, 90% D$_2$O. These spectra demonstrated clearly that the isomer first isolated by HPLC and characterized was the 3'-isomer on the basis of a set of complete COESY cross-peaks and a NOE between the acetyl methyl group and the peak assigned to H3'. Conversion of 3'- to 2'-isomers reached a 67:47 equilibrium and the 2'-isomer was characterized in a sample containing both 2'- and 3'-isomers. The 2'-assignment was made with a complete set of COESY cross peaks and a NOE between the acetyl methyl groups and the peak assigned to H2' (FIG. 9).

Figure 4:
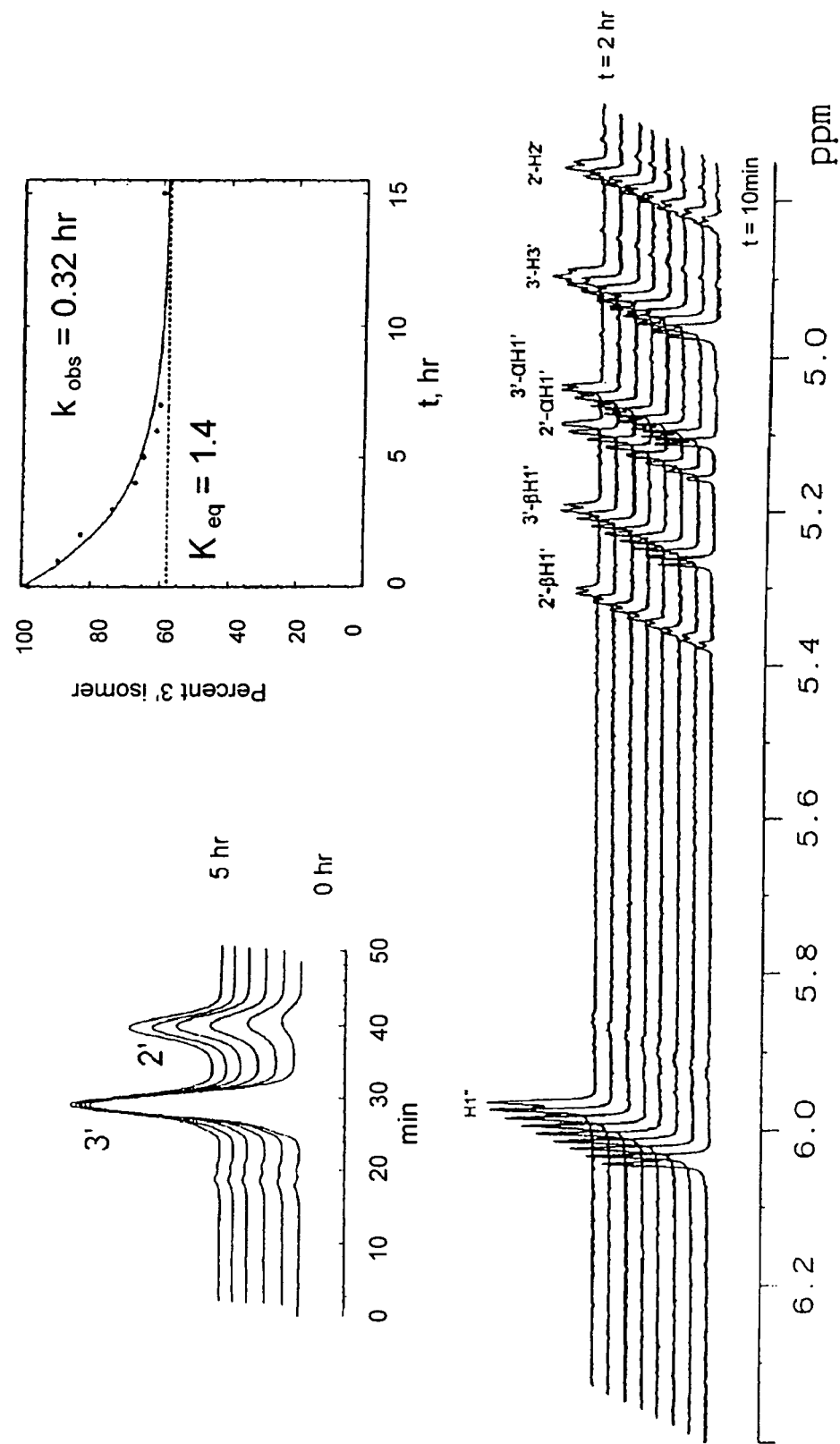
FIG. 4 shows plots and a chromatogram relating to the structure of AADPR. Upper left panel: Time dependence of HPLC chromatograms showing conversion of 3'-AADPR to 2'-AADPR isomer over 5 h at 15° C. Lower panel: Stack plot of 1D $^1$H NMR spectra showing changes in 3' (α and β) AADPR (major) and 2' (α and β) AADPR (minor) regioisomer populations as a function of time at 10° C. Upper right panel: Plot of 3' O-acetyl-ADPR isomer as a function of time at 15° C. as measured by HPLC. Solid curve represents best fit to the first order function described in the text. The dotted line represents the equilibrium determined by integration of HPLC peak areas after 24 h incubation.

NMR and HPLC methods demonstrated interconversion of 3'- to 2'-isomers to provide an equilibrium mixture at 15° C. and 20° C., respectively. Stack plots for both methods (FIG. 4) were fit to an exponential decay curve and allowed determination of the first-order rate constant for acetyl migration $k_{3' \, to \, 2'}$ of 0.32 h$^{-1}$ (FIG. 4, upper panel). The equilibrium constant K was found to be 1.4 at 15° C., based upon HPLC peak integrations of the 2'- and 3'-isomers. The calculated value for $k_{3' \, to \, 2'}$ was thus 0.45 h$^{-1}$. A full equilibrium and kinetic description of acetyl migration including the equilibria for the anomeric forms is shown in Scheme 1B of FIG. 8.

Order of production of the 2'- and 3'-isomers. The order of AADPR regioisomer generation by Sir2p was established in an $^1$H NMR experiment at 5° C. (see methods). The stacked spectra (FIG. 5) reveal that the 2' isomer builds up early in the reaction followed by production of the 3' isomers. Each peak from the C1-H α at and β forms of the respective regioisomers was well resolved. This result establishes that the kinetic sequence for AADPR production is 2' before 3' (Scheme 1C of FIG. 8). The rate of Sir2p catalysis exceeds the rate constant for interconversion with a ratio $k_{cat}/k_{2'-3'}$ of 20 at 5° C.

Incorporation of $H_2^{18}O$ into product. Reaction stoichiometry for Sir2p (Scheme 1C of FIG. 8) indicates that two new oxygen atoms are incorporated into AADPR. It has been assumed that one or more of these oxygen atoms comes from water[14,16,18]. The Sir2p deacetylation reaction can be viewed as a hydrolysis reaction yielding amino lysine and acetate coupled to an ADP-ribosyl transfer reaction where ADPR is transferred to acetate.

Figure 5:
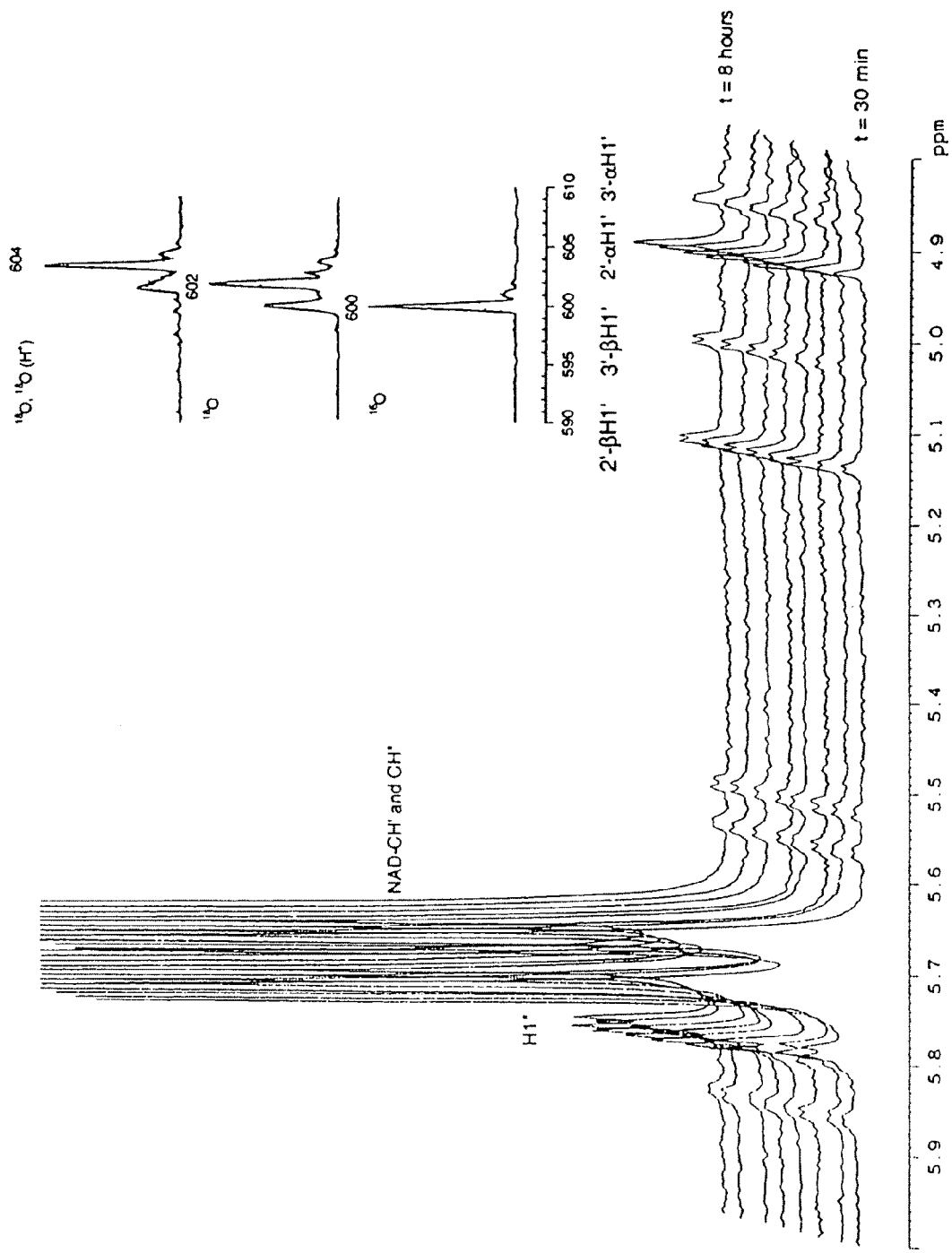
FIG. 5 shows a stack plot of 1D $^1$H NMR spectra (600 MHz) taken at 5° C., showing initial formation of 2'-AADPR (resonances at d 5.15 (2'β), and 4.93 (2'α)) catalyzed by 50 mM Sir2Af2 in the presence of 10 mM NAD+, and 1.5 mM JB12 peptide. Later time points illustrate conversion of 2'-ADPR to 3'-ADPR (resonances at d 5.04 (3'β), and 4.88 (3'α)). Spectra are separated in time by 1.0 hour. Inset: MS spectra of molecular ions of AADPR derived from Sir2Af2 reactions after treatment with isotope labeled water in reaction and/or in quench. Top panel shows ions derived from a Sir2Af2 reaction in $^{18}O$ water followed by a $H_2^{18}O$ quench containing 10% $d_4$-acetic acid for 3 h at room temperature. Middle panel shows ions derived from the Sir2Af2 reaction in $^{18}O$ water without quenching. Bottom panel shows ions derived from the Sir2Af2 reaction in unlabeled water without quenching. Results for other conditions and experimental details are listed in Table 2 and Table 2 legend.

Reactions in $^{18}O$ water followed by MS analysis of the AADPR product indicated that product mass is increased by 2 amu consistent with incorporation of a single $^{18}O$ from water into AADPR. The $^{18}O$ enrichment (65%) was the same as the initial $^{18}O$ content in the water assay (FIG. 5, inset). Dilution of the samples in 2 vol of $^{16}O$ water at pH 7.5 or in 10% $d_4$-acetic acid followed by MS analysis (time range 30 min-24 h) showed that $^{18}O$ content did not change (Table 2). The site of $^{18}O$ incorporation is therefore a non-exchangeable oxygen atom in the 2'-AADPR and 3'-AADPR molecules.

The $^{18}O$ atom could reside in either the acetate moiety of 2'- and 3'-AADPR molecules or in the 1'-OH of the product. Incubation of unlabeled ADPR and 2'- and 3-AADPR in $^{18}O$ in 10% $d_4$-acetic acid for three h at room temperature increased mass by 2 amu consistent with incorporation of a single $^{18}O$ into the molecules, but in neutral conditions no such change in mass was observed. Only the 1'-OH is consistent with this exchange. 2'- and 3'-AADPR derived from $^{18}O$-containing Sir2p reactions when incubated with 10% $d_4$-acetic acid and $^{18}O$ water incorporated a second $^{18}O$ into the AADPR molecule (mass=604) consistent with isotope exchange of the 1'-OH and demonstrating the presence of a free hydroxyl (FIG. 5, inset).

Exchange experiments were combined with MS/MS studies and reinforced this chemical interpretation (Table 2). Acid catalyzed exchange reactions of 2'- and 3'-AADPR in $^{18}O$ water gave a 542 amu fragment, consistent with incorporation of a single $^{18}O$ into the ribose moiety. Reactions of Sir2p run in either $^{16}O$ or $^{18}O$ water led to 540 amu fragments that originate from loss of acetate. Thus the non-exchangeable $^{18}O$ atom obtained from solvent is incorporated into the carbonyl oxygen of 2'- and 3'-acetates.

TABLE 2

Mass Spectrometry: observed species in the presence of $^{18}O$ and $^{16}O$ water

| Reaction conditions | Quench conditions | Molecular Species (m/z) | Fragmentations (major species) |
|---|---|---|---|
| $^{16}O$ | NQ | 600 | 540, 346 |
| $^{18}O$ | NQ | 602 | 540, 346 |
| $^{16}O$ | $^{18}O$, H$^+$ | 602 | 542, 346 |
| $^{18}O$ | $^{18}O$, H$^+$ | 604 | 542, 346 |
| $^{18}O$ | $^{16}O$, H$^+$ | 602 | 540, 346 |
| ADPR | $^{18}O$, pH 7.5 | 558 | 346 |
| ADPR | $^{18}O$, H$^+$ | 560 | 346 |

TABLE 2-continued

Mass Spectrometry: observed species in the presence of $^{18}O$ and $^{16}O$ water The reaction conditions for the first five entries reflect Sir2Af2 mediated deacetylation at pH 7.8, 50 mM potassium phosphate at 55° C. for 30 min with enrichment of the reaction water content (minimal 65%) with the isotope shown. The reaction was subsequently analyzed by LCMS in MS and MS/MS modes. The molecular species reflects the observed major ion identified at 7 min, the retention time of AADPR in LC. Fragmentations are based upon MS/MS spectra derived from selection of the major molecular ion. Not quenched (NQ) reflects injection of otherwise untreated reaction mixtures. In cases where a quench was used, 2 volumes of either 95% $H_2^{18}O$ or unlabeled water containing 10% $d_4$-acetic acid was added to reaction mixtures after initial 55° C. incubation and reacted for 3 h at room temperature. Samples were subsequently analyzed by LCMS and MS/MS. The bottom two cases reflect behavior of ADPR in either 50 mM potassium phosphate pH 7.5 or 95% $H_2^{18}O$ containing 10% $d_4$-acetic acid after incubation for a three hour period at room temperature.

Inhibitor ara-F-NAD$^+$ substrate reaction, exchange and inhibition. Ara-F-NAD$^+$ is a powerful inhibitor for many ADP-ribosyltransfer enzymes[26], since the substitution of fluorine for OH at the 2' position makes ara-F-NAD$^+$ roughly 50 times more stable than NAD$^{+2 6}$ and thus permits the chemical trapping of enzyme-ADP-ribose covalent intermediates[27]. Ara-F NAD$^+$ did not serve as a substrate in deacetylation or exchange reactions. Controls readily exchanged radiolabeled nicotinamide (5 mM) into ara-F-NAD$^+$ and Sir2p exchanged nicotinamide into 50 μM NAD$^+$ under these conditions. Ara-F-NAD$^+$ did not inactivate Sir2p in the presence or absence of peptide dispite its activity on the control using CD38. Thus, ara-F-NAD$^+$ is inert in the Sir2p reaction.

DISCUSSION

We show here that acetylated human p53 tumor suppressor and peptides derived from it are excellent in vitro substrates for a wide variety of Sir2ps. Because acetylation is required for activation of efficient sequence-specific DHA binding, deacetylase action is predicted to decrease p53 activity in cells. Previous studies have shown a complex relationship between p53 and the Rpd3 family of deacetylases. p53 acts as a repressor at certain loci, and the Rpd3 histone deacetylase-associated factor, Sin3p, mediates such repression[37]. Paradoxically, one study suggests that p53 itself can be a a substrate for Rpd3 family deacetylases, at least when overexpressed[38]. Deacetylation of p53 by Sir2ps would allow its activity to be modulated indirectly via cellular metabolic or redox states. This would make sense, particularly following oxidative stresses, which are associated with DNA damage. However, our studies do not indicate any specificity among Sir2 proteins for p53. Those enzymes that efficiently deacetylate histones work well on p53 as well—even if they are derived from Archaea. Recent work from other laboratories also shows that acetylated BSA, a non physiologic substrate, is a substrate for Sir2af1[18]. Thus, if Sir2ps play regulatory roles in modulating p53 activities, there must be unidentified factors or conditions to make such NAD$^+$-regulated deacetylation reactions specific.

Product of Sir2p. The identification of 2'-AADPR as the product of Sir2p deacetylation has reinforced the view that Sir2ps represents a unique type of NAD$^+$-dependent enzyme. The product of Sir2p has been proposed to be β-1'-AA DPR[15,17] and the X-ray crystal structure of Sir2p from Min et al.[18] was interpreted in terms of formation of this species. This product was suggested from the precedent of other ADP-ribosyl transferases that also catalyze nicotinamide exchange reactions similar to the Sir2p reaction. NAD$^+$ glycohydrolases and CD38 both form products with β-configuration and both catalyze base-exchange reactions. Thus the proposal for the Sir2p product was a logical extension of known enzymology[15,17]. Base exchange requires enzyme stabilization of an ADPR electrophile, or formation of a covalent enzyme intermediate[27], normally resulting in ADPR transfer to nucleophiles with 1-β-stereochemistry. We synthesized authentic β-1'-AADPR and established that none of the product formed by Sir2p corresponds to this compound. The stability observed for β-1'-AADPR also establishes that it is not an intermediate in the Sir2p reactions. The product released from the catalytic site of Sir2p is 2'-AADPR which forms a Sir2p-independent mixture of 2'- and 3'-acetyl isomers. The chemical exchange of the acetyl group results in a nearly 2':3' equilibrium ratio of 67:47 at 15° C. The exchange occurs at rates of 0.45 hr$^{-1}$ and 0.32 hr$^{-1}$ at this temperature. At physiological temperatures of 37° C., the equilibrium will be established within 60 min. Thus, it is conceivable that a cascade downstream of Sir2p action could be timed by the spontaneous conversion of 2'- to 3'-AADPR. Each regioisomer exist in 1' α and β anomeric forms, generating four distinct species by NMR (Scheme 1B of FIG. 8). The α/β anomeric equilibrium is fast (>50 s$^{-1}$).

Sir2p catalyzed steps that generate 2'-AADPR. The formation of 2'-AADPR requires that the 2'-hydroxyl act as a nucleophile at some stage of the chemical mechanism. Participation of the 2'-hydroxyl has been suggested. The 2'-hydroxyl was proposed to act directly as the nucleophile to deacetylate the amide moiety[16]. The direct 2'-nucleophile mechanism requires incorporation of $^{18}$O from solvent water at the 1'-position as the sole $^{18}$O label in the 2'-AADPR released from Sir2p. However, MS analysis established that $^{18}$O appears in the acetyl group, therefore action of the 2'-hydroxyl group as the primary nucleophile can be eliminated.

To reconcile the coupling of ADPR transfer with deacetylation, the reaction can be compared to the ADP-ribosyltransfer reactions catalyzed by the ADP-ribosylating toxins in which the enzymes generate a highly reactive ADP-ribooxocarbenium ion that is attacked by a weak nucleophile. For example, in cholera toxin, ADPR is transferred from NAD$^+$ to an Arg with stereochemical inversion of the ADP-ribose to generate a α-1'-substituted ADPR-amidate[39]. This same strategy in the Sir2p reaction generates the ADP-ribo-oxocarbenium ion that captures the acyl oxygen of the N-acetyl-lysine to generate an O-alkyl-amidate (Scheme 1D of FIG. 8). O-Alkyl-amidates are chemically activated and spontaneously hydrolyze in water to form free amines and esters[40,41]. For Sir2p these correspond to the deacetylated lysine and the α-1'-AADPR. Transition state studies of all ADP-ribose transfer reactions thus far characterized show that a powerful ribo-oxocarbenium ion electrophile is generated to facilitate ADPR transfer chemistry[42].

This mechanism explains the requirement of the peptide substrate for nicotinamide exchange; even in mutagenized enzymes that lack deacetylase activity[18]. There are two possible reaction pathways that can form 2'-AADPR. In the first, the intermediate O-alkyl-amidate hydrolyzes to a 1'-substituted α-AADPR that isomerizes to 2'-regiochemistry to give the observed product (Mechanism A of FIG. 7; Scheme 1D of FIG. 8). Alternatively, the 2'-hydroxyl could attack the O-alkyl-amidate intermediate to generate a cyclic acyloxonium, followed by hydrolysis to form the observed 2'-AADPR product (Mechanism B of FIG. 7; Scheme 1E of FIG. 8).

Nature of the α-1'-AADPR intermediate. Low temperature NMR studies performed at 5° C. using Sir2Af2 furnished no evidence for accumulation of α-1'-AADPR. Therefore, conversion of α-1'-AADPR to 2'-AADPR occurs >the catalytic rate of the enzyme, since the detection level for the α-1'-AADPR was near the enzyme concentration. The 2'- to 3'-AADPR interconversion is slower than $k_{cat}$ by a factor of 20 and enzyme-dependent production of the 2'-isomer was observed by NMR (FIG. 4). The mechanism most consistent with the results is the 2'-hydroxyl attack on the 1'-O-alkylamidate to form a 1'-2' substituted acyl-oxonium structure as the precursor to 2'-AADPR formation on the enzyme (Mechanism B of FIG. 7; Scheme 1E of FIG. 8).

Label pattern from H$_2$$^{18}$O incorporation. Water was confirmed as a participant in the catalytic mechanism by incorporation of a single $^{18}$O atom from $^{18}$O water in the AADPR product. This oxygen atom is a nonexchangeable oxygen of the acetyl group. Confirmation of the single water molecule mechanism and of an acid-exchangeable oxygen at the C1'-hydroxyl confirm an acyl-Oxygen-C1' bond formation and the attack of water at the carbon of the amide carbonyl.

Figure 6:
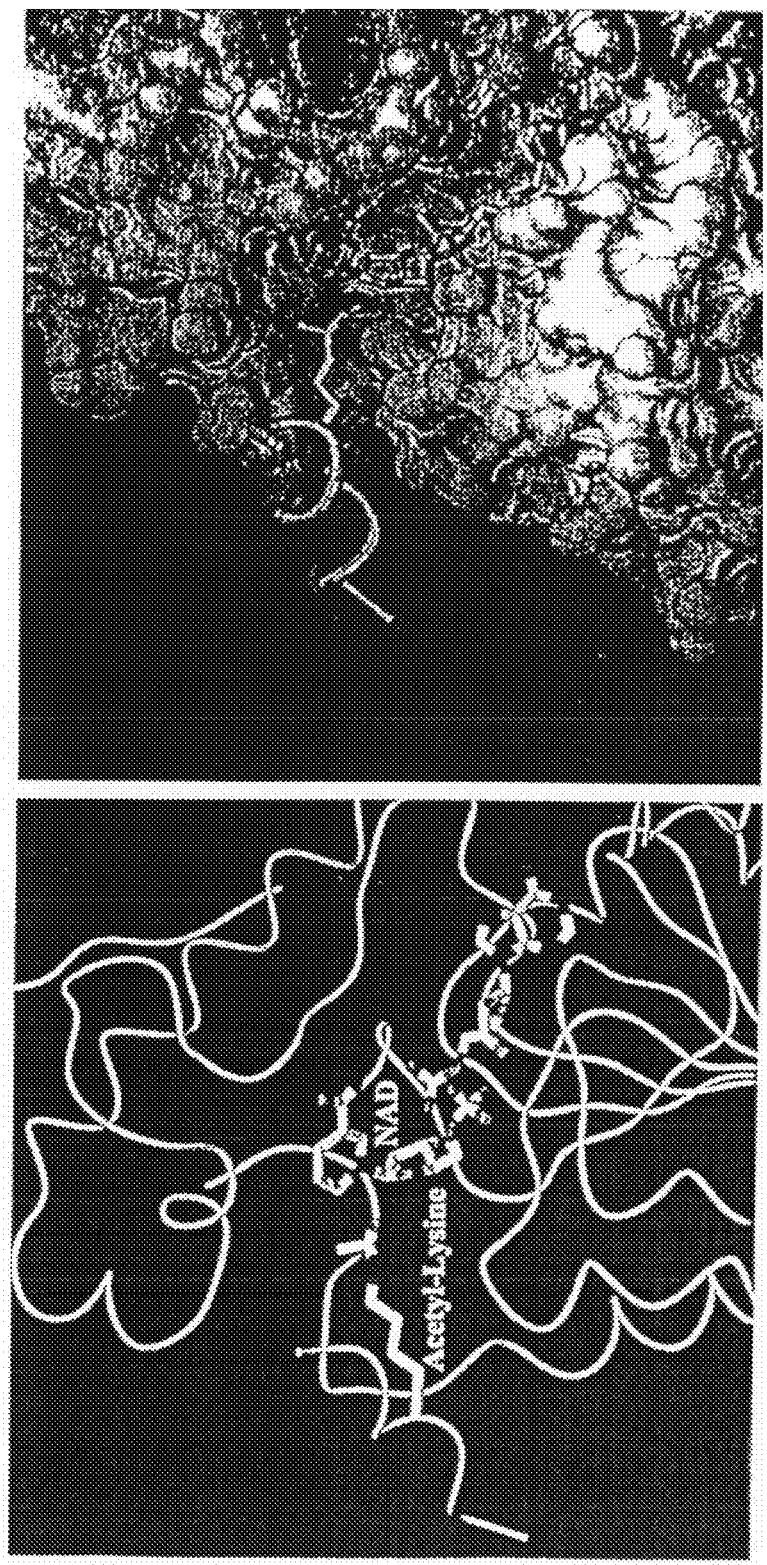
FIG. 6 shows two graphics showing the acetyl-lysine sidechain, docked into the active site cavity of Sir2Af118. Left and right panels are peptide backbone and space filling models, respectively. The acetyl-oxygen from the N-acetyl-lysine at residue 382 is within van der Waals contact of C1' of NAD+.

X-ray structure is consistent with formation of observed products. Initial inspection of the Sir2-Af1 X-ray structure[18] shows that there are no putative nucleophilic residues within bonding distance of NAD$^+$ to support a covalent ADPR transfer and a β-stereochemical outcome. A fresh view of the structure in light of our experimental results is intriguing, as the α face of the NAD$^+$ is unencumbered from attack by a bound acetyl and the 2'-hydroxyl is found unligated to any side chain in the enzyme. Indeed, a modeling study allowed facile docking of the p53 C-terminal peptide NMR structure into the crystal structure of Sir2Af1 (FIG. 6). In this model, the acetyl oxygen is indeed perfectly positioned to approach the α face of the nicotinamide bound to Sir2Af1. Furthermore, the histidine located near the 3' hydroxyl has been shown by mutagenesis to be essential for deacetylase function, suggesting that the bottom face of the NAD$^+$ molecule is subject to acid-base transfer pathways to fulfill catalytic function.

Summary of the Sir2p mechanism. The sum of these results provides strong support for the reaction steps of Scheme 1E of FIG. 8. Most histone deacetylases are simple hydrolases—hydrolysis of N-acetyl groups is a chemically simple and energetically favorable reaction. Biological rationales for consumption of metabolically valuable NAD$^+$ as a cosubstrate may include substrate signaling; NAD$^+$ levels may signal cellular energetic and redox states to control Sir2p-based gene regulation. A second possibility is that the reaction initiates a Sir2p signal transduction pathway by generation of the novel compounds 2'- and 3'-AADPR. These molecules have not been previously recognized in metabolism, and carry the features of chemical instability common to other initiators of signaling pathways. Recent evidence that some Sir2p homologues are cytosolic[35,36] and can accept acetyl groups from other non-histone proteins such as chemically acetylated BSA[18] or p53, suggest a much broader role in cell development and transcriptional regulation by acetyltransferase reactions. Identification of the products of Sir2p provides the tools for further investigations of these pathways and provides information for inhibitors designed specifically for this unusual ADP-ribosyl-transferase.

Example 2

Improved Assays for Sir2 and Inhibitors of SIR2

As discussed above, the reaction of Sir2 with NAD$^+$ and an appropriate protein or peptide acetyl donor produces 2' and 3'-O-acetyl-ADPR (AADPR) and deacetylated protein or peptide. The detection of Sir2 activity can be effectively performed by measuring the production of the AADPR product. Previous methods for this were based upon the use of HPLC to detect products. By radiochemical labeling of NAD$^+$ by known methods the production and quantitation of radiolabeled AADPR was achieved by the rapid separation of AADPR from unreacted NAD$^+$ on Sephadex-DEAE columns.

The method as practiced is as follows:

300 μL of 50 mM potassium phosphate buffer pH 6.2 (or 7.0 or 7.5) containing 150 μM of the peptide JB12 (p53 based) and 150 mM [5'-$^{14}$C]NAD$^+$ (specific activity 100000 cpm per sample) were reacted with 3 μg Sir2 enzyme in 5 μL buffer (yeast homologue Sir2p or *Archaeglobus fulgidus* AF2Sir2) for a period varying from 30 min to 4 h. Upon completion of reaction time 50 μL aliquots of reaction mixture were frozen on dry ice. After 4 h all tubes were thawed and loaded onto 1 mL DEAE. Sephadex columns pre-equilibrated with 25 mM ammonium acetate pH 7.0. 6 mL of 25 mM ammonium acetate was eluted through the columns and collected in 1 ml fractions. The column was subsequently eluted with 6 mL 500 mM ammonium acetate and again collected in 1 mL fractions. Each column fraction was counted by addition of 9 mL scintillation fluid and placed into a scintillation counter. The profiles for the elutions are shown in FIG. 11. Using this method, the unreacted NAD$^+$ elutes first (fractions 1-6), followed by AADPR (fractions 7-12). The sum of the fractions above 100 cpm were subtracted with the 0 time counts (FIG. 12). The sensitivity for detection of AADPR versus NAD is 5 μM in 50 μL, in other words, 250 pmoles of AADPR.

This method has numerous applications to the detection of Sir2 activity in biological extracts when combined with controls for the non-Sir2 degradation of NAD$^+$. We have showed that extracts containing Sir2, when combined with a suitable acetyl donor substrate, can produce AADPR, and that activity can be directly measured by formation of AADPR via the above-described column methodology. Detection of AADPR in bacterial extracts expressing Sir2 activity was performed analogously to that stated above, except that instead of adding pure enzyme, whole cell homogenates were added. Controls using uninduced cells, or cells induced to produce a mutant inactive Sir2 showed no production of AADPR, as determined by this assay, and no breakdown of NAD$^+$ occurred. The sensitivity of this assay allows for detections of AADPR that are presumably near biologically relevant concentrations (5 μM).

The advantages of this method are the speed of the assay, which requires only 4-7 hours for up to 20 samples, and its reliance upon direct detection of AADPR, a unique product of the Sir2 reaction. This method also permits the facile purification of a pure form of AADPR, as the separation conceived also functions to separate AADPR from other components in reaction mixtures. Purified AADPR from cellular Sir2 action can then be verified in chemical structure by HPLC or MS, or used in another specific assay.

Further applications of this method include the evaluation of inhibitors of Sir2 activity. The discovery and quantitative evaluation of the action of small molecules on Sir2 action has the potential to lead to therapeutic compounds. Utilization of AADPR to detect Sir2 inhibition relies upon detecting the sole unique product of Sir2 action in cells. In this method the reaction is performed as described above, with the potential inhibitor being added in varying concentrations. Reaction rate for Sir2 is determined in each sample by using the initial linear phase of reaction progress, which is fastest and is equal to the slope. Inhibitors of the reaction show decreased rates. Inhibition is quantified by the equation $$1/v = 1/V_{max}(1+[I]/K_{ii}) + K_m/V_{max}(1+[I]/K_i)$$

where $K_m$ and $V_{max}$ are parameters used to describe the Michaelis constants of the substrate that is subject to competitive binding with the inhibitor, [I] is the inhibitor concentration and $K_i$ and $K_{ii}$ are the competitive and non-competitive binding constants. This method would be expected to discover competitive inhibitors with $K_i$ values with binding affinities as high as 1 mM, and practically can identify inhibitors with binding affinities in the range of 100 μM or below. In one embodiment, the method comprises the addition of 200 μM inhibitor to 300 μL reaction mixtures containing 100 μM of NAD$^+$ and peptide substrate.

Investigations of several extracts, including hamster ovary cells and rat liver has shown that high esterase activity exists that can breakdown AADPR to ADPR and acetate. The use of AADPR or radiolabeled AADPR is a strategy to characterize and discover the esterases (or other enzymes) that break down or utilize AADPR in vivo. Specifically, AADPR breakdown can be measured by HPLC or TLC assay. When radiolabels are used, amounts of AADPR necessary for this purpose can be as small as 250 pmoles.

As with the production of AADPR, the use of an AADPR-based method of detecting AADPR breakdown furnishes the unique Sir2 reaction product as a means to interrogate the activities that utilize the compound in cells. Quantifying breakdown versus time provides a method to discover not only the AADPR utilizing activities but also compounds that can inhibit this activity. Inhibition of AADPR breakdown in cells by small molecule compounds can increase AADPR action in cells, thus extending Sir2 effects, via the increased lifetime of the only unique product of Sir2 action inside of cells.

Esterase activity of DEAE separated rat liver extract as measured by para-nitrophenol release from para-nitrophenylacetate (400 nm) is shown in FIG. 3. This shows the inherent esterase rich background to which AADPR is subject in liver cells. The use of AADPR as a substrate to interrogate this broad esterase activity can be used to determine AADPR specific esterases inside of cells. One strategy is to use the ratio of AADPR esterase activity/para-nitrophenylacetate esterase activity as a measure of specificity of the activity for the AADPR product measured against a generic substrate activity. Enzymological theory posits that enzyme activity is optimized for the substrate for which the enzyme was designed. Thus, activity ratios should be highest for enzymes that are designed to recognize AADPR.

Other strategies can also be employed, such as using small molecule inhibitors that resemble AADPR. As shown in FIG. 13, the esterases are sensitive to mM concentration additions of AADPR analogs.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of determining whether a test compound is an inhibitor of a Sir2 enzyme, the method comprising
combining the test compound with the Sir2 enzyme, $NAD^+$ and an acetylated peptide substrate of Sir2 in a reaction mixture under conditions and for a time sufficient to deacetylate the peptide in the absence of the test compound;
quantifying 2'/3'-O-acetyl-ADP-ribose produced from the acetylated peptide; then
comparing the quantity of 2'/3'-O-acetyl-ADP-ribose produced with a quantity of 2'/3'-O-acetyl-ADP-ribose produced under the same conditions but without the test compound;
wherein the presence of less 2'-O-acetyl-ADP-ribose and/or 3'-O-acetyl-ADP-ribose than without the test compound indicates that the test compound is an inhibitor of the Sir2 enzyme.

2. The method of claim 1, wherein the 2'/3'-O-acetyl-ADP-ribose is quantified after subjecting the reaction mixture to chromatography.

3. The method of claim 2, wherein the chromatography is HPLC.

4. The method of claim 2, wherein the chromatography is on a Sephadex-DEAE column.

5. The method of claim 1, wherein the $NAD^+$ is radiolabeled such that the 2'/3'-O-acetyl-ADP-ribose is radiolabeled after the peptide is deacetylated.

6. The method of claim 5, wherein the $NAD^+$ is radiolabeled at the 5' position with $^{14}C$.

7. The method of claim 1, wherein the acetyl group on the acetylated peptide is radiolabeled.

8. The method of claim 1, wherein the acetylated peptide substrate consists at least two amino acids, wherein at least one of the amino acids comprise a lysine residue that is acetylated at the $\epsilon$-amino moiety.

9. The method of claim 8, wherein the acetylated peptide substrate consists of at least three amino acid residues.

10. The method of claim 8, wherein the acetylated peptide substrate consists of at least five amino acid residues.

11. The method of claim 8, wherein the acetylated peptide substrate consists of at least ten amino acid residues.

12. The method of claim 8, wherein the acetylated peptide substrate consists of at least fifteen amino acid residues.

13. The method of claim 8, wherein the acetylated peptide substrate consists of at least eighteen amino acid residues.

14. The method of claim 1, wherein the acetylated peptide substrate is homologous to an acetylated region of a regulatory domain of a p53.

15. The method of claim 14, wherein the acetylated peptide comprises JB11 or JB12.

16. The method of claim 15, wherein the acetylated peptide substrate is an acetylated p53.

17. The method of claim 1, wherein the acetylated peptide substrate is homologous to an acetylated region of a histone.

18. The method of claim 17, wherein the acetylated peptide is an acetylated histone.

19. The method of claim 1, wherein the Sir2 enzyme is derived from a prokaryote.

20. The method of claim 19, wherein the Sir2 enzyme is derived from an archaeal bacterium.

21. The method of claim 19, wherein the Sir2 enzyme is derived from a eubacterium.

22. The method of claim 1, wherein the Sir2 enzyme is from a eukaryote.

23. The method of claim 22, wherein the Sir2 enzyme is from a yeast.

24. The method of claim 22, wherein the Sir2 enzyme is from a human.

* * * * *

UNITED STATES PATENT AND TRADEMARK OFFICE
CERTIFICATE OF CORRECTION

| | | |
|---|---|---|
| PATENT NO. | : 7,741,295 B2 | Page 1 of 1 |
| APPLICATION NO. | : 12/231880 | |
| DATED | : June 22, 2010 | |
| INVENTOR(S) | : Vern L. Schramm et al. | |

It is certified that error appears in the above-identified patent and that said Letters Patent is hereby corrected as shown below:

In the Specification

Column 1, lines 15-20, should read:

-- STATEMENT OF GOVERNMENT SUPPORT

This invention was made with government support under grant number AI034342 awarded by the National Institutes of Health. The government has certain rights in the invention. --

Signed and Sealed this
Twenty-second Day of December, 2015

Michelle K. Lee
*Director of the United States Patent and Trademark Office*